US011944398B2

(12) United States Patent
 Abbott

(10) Patent No.: US 11,944,398 B2
(45) Date of Patent: Apr. 2, 2024

(54) SURGICAL INSTRUMENT ACTUATION MECHANISMS

(71) Applicant: Intuitive Surgical Operations, Inc., Sunnyvale, CA (US)

(72) Inventor: Ryan Charles Abbott, San Jose, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 574 days.

(21) Appl. No.: 17/042,743

(22) PCT Filed: Mar. 28, 2019

(86) PCT No.: PCT/US2019/024569
§ 371 (c)(1),
(2) Date: Sep. 28, 2020

(87) PCT Pub. No.: WO2019/191420
PCT Pub. Date: Oct. 3, 2019

(65) Prior Publication Data
US 2021/0022815 A1    Jan. 28, 2021

Related U.S. Application Data

(60) Provisional application No. 62/650,115, filed on Mar. 29, 2018.

(51) Int. Cl.
  *A61B 34/35*    (2016.01)
  *A61B 17/00*    (2006.01)
  (Continued)

(52) U.S. Cl.
  CPC ........ *A61B 34/35* (2016.02); *A61B 17/00234* (2013.01); *A61B 34/71* (2016.02);
  (Continued)

(58) Field of Classification Search
  CPC .... A61B 17/00234; A61B 2017/00477; A61B 2034/302; A61B 2090/064;
  (Continued)

(56) References Cited

U.S. PATENT DOCUMENTS 3,145,333 A * 8/1964 Pardini ................. G21C 19/02
                                                    901/34
2005/0021018 A1   1/2005 Anderson et al.
(Continued)

FOREIGN PATENT DOCUMENTS

WO    WO-2017205333 A1    11/2017

OTHER PUBLICATIONS

International Search Report and Written Opinion for Application No. PCT/US2019/024569, dated Jul. 8, 2019, 13 pages.
(Continued)

*Primary Examiner* — Mohamed G Gabr
(74) *Attorney, Agent, or Firm* — MARSHALL, GERSTEIN & BORUN LLP

(57) ABSTRACT

Systems and methods for computer-assisted systems using robotic technology are described. For example, this disclosure describes systems and methods that can be used in various contexts such as, but not limited to, minimally invasive computer-assisted tele-operated surgery using robotic technology. The disclosure describes instruments and mechanisms for actuating and controlling the motions of such instruments. The instruments and actuator mechanisms may be used in medical operations and non-medical operations.

16 Claims, 28 Drawing Sheets

(51) Int. Cl.
*A61B 34/00* (2016.01)
*A61B 34/30* (2016.01)

(52) U.S. Cl.
CPC .............. *A61B 2017/00477* (2013.01); *A61B 2034/302* (2016.02)

(58) Field of Classification Search
CPC ........ A61B 2090/371; A61B 2090/372; A61B 34/30; A61B 34/35; A61B 34/70; A61B 34/71
See application file for complete search history.

(56) References Cited

U.S. PATENT DOCUMENTS

| | | | |
|---|---|---|---|
| 2013/0296886 A1* | 11/2013 | Green | B25J 15/04 606/130 |
| 2014/0277333 A1 | 9/2014 | Lewis et al. | |
| 2015/0080924 A1 | 3/2015 | Stulen et al. | |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

\* cited by examiner

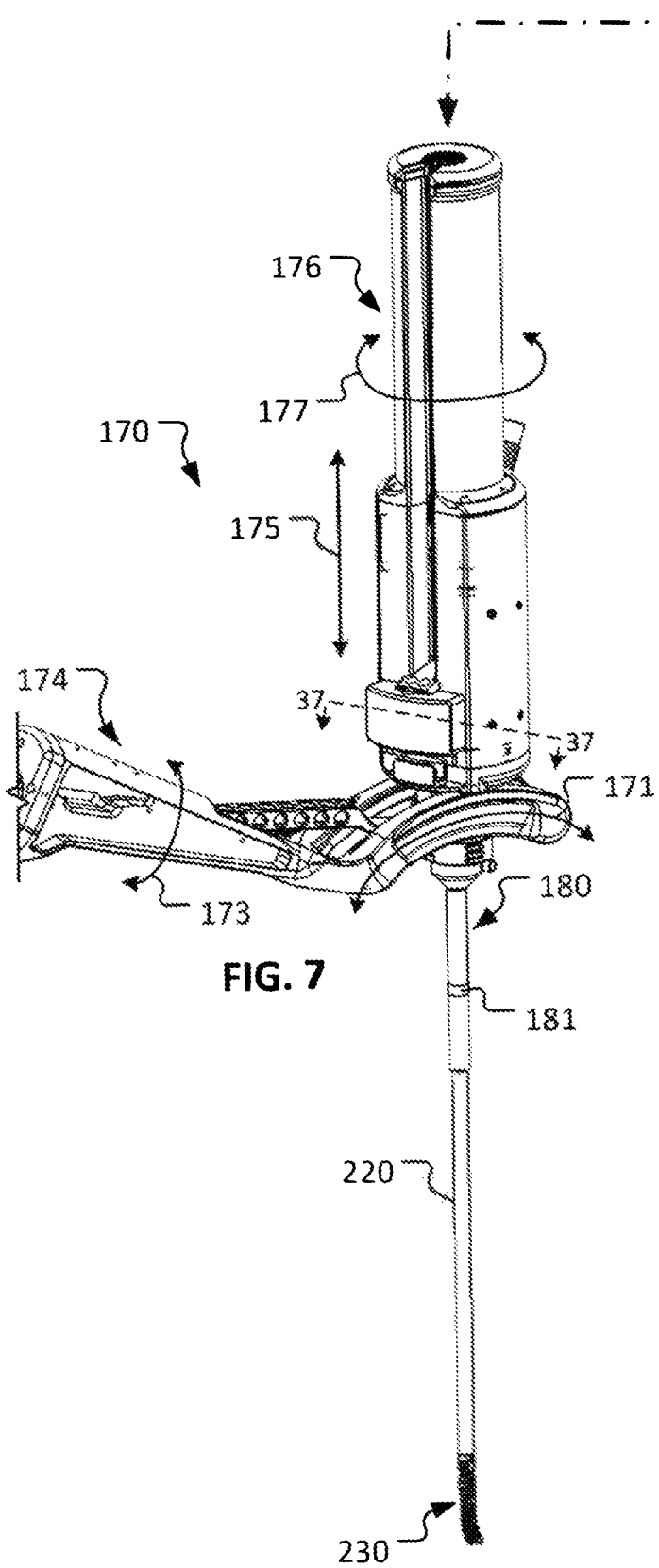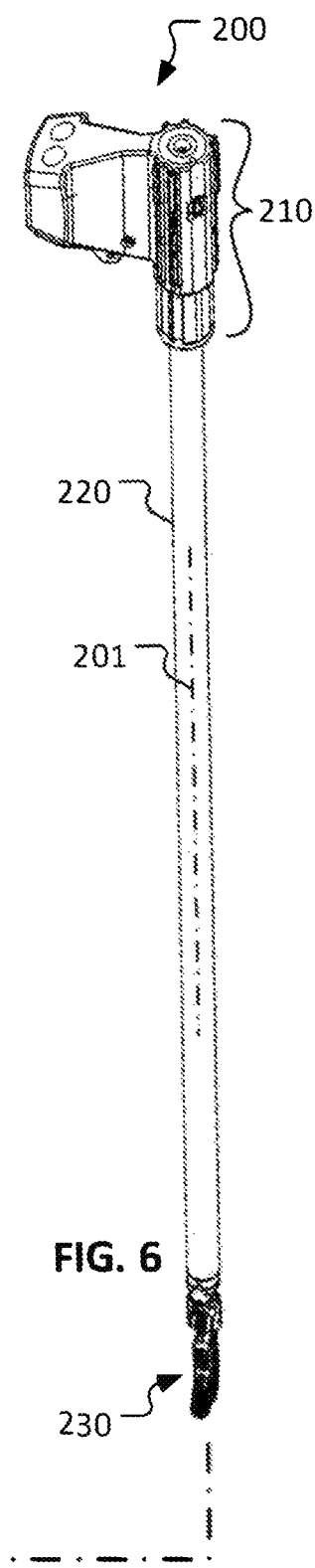
FIG. 7
FIG. 6

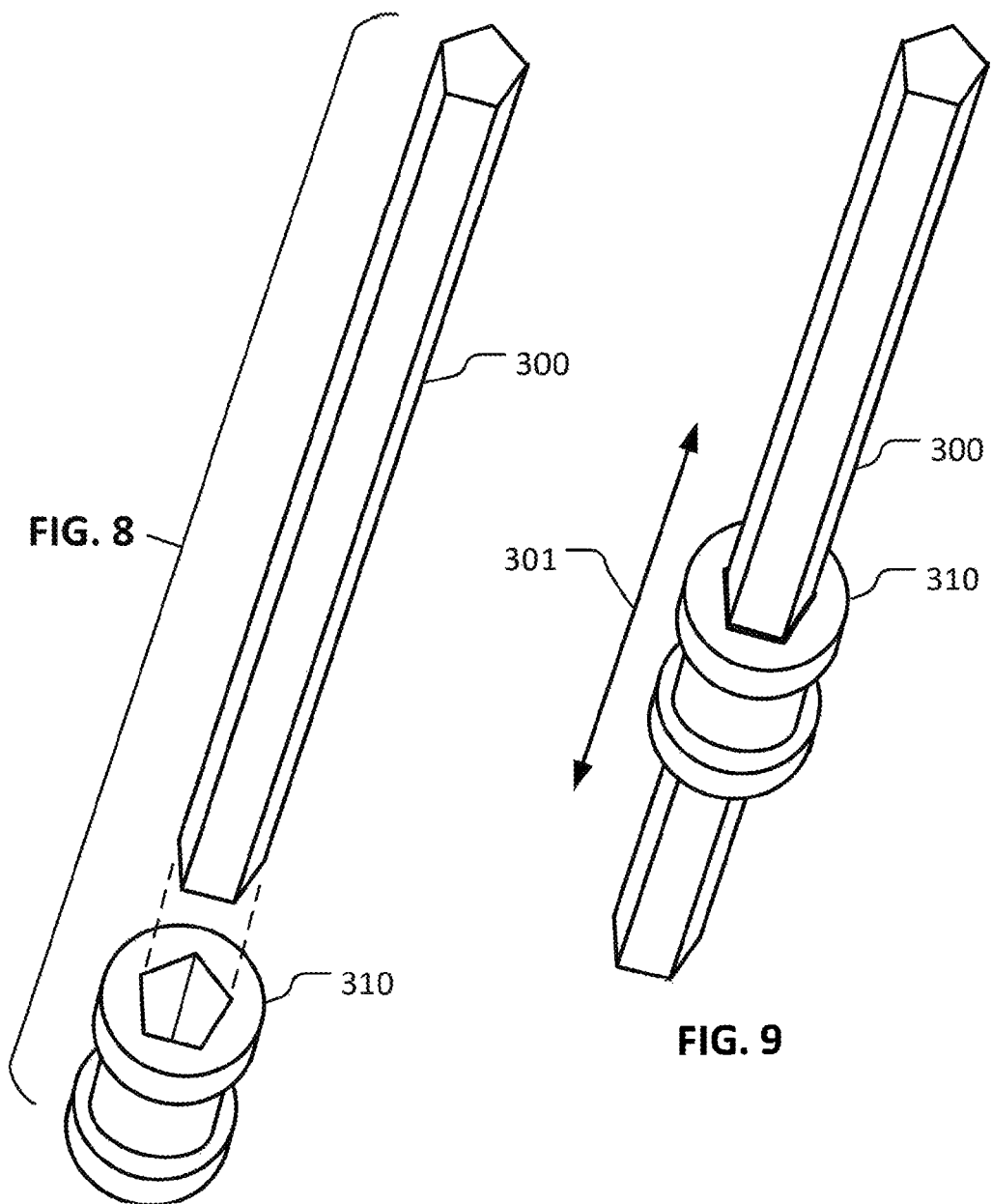

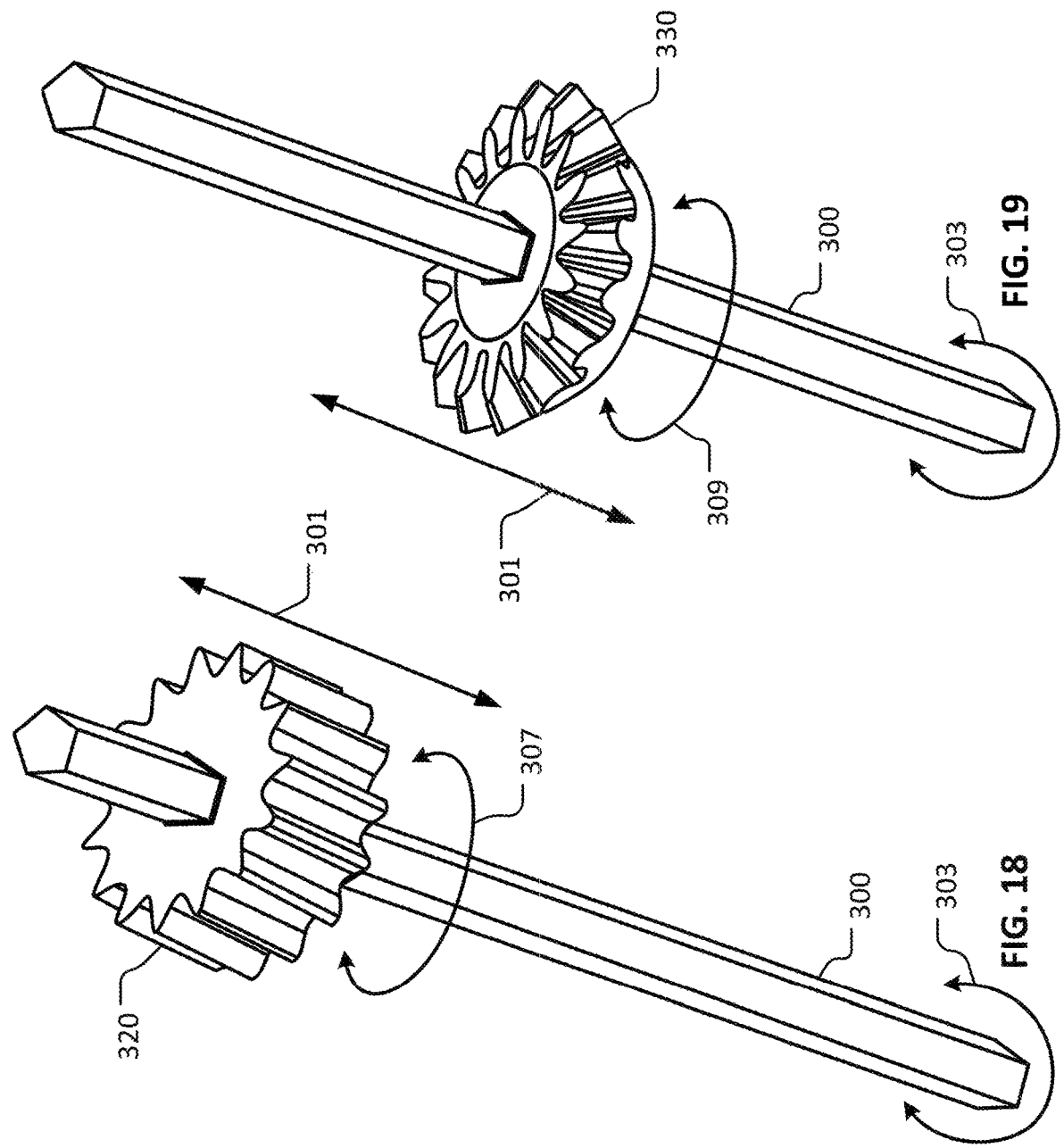

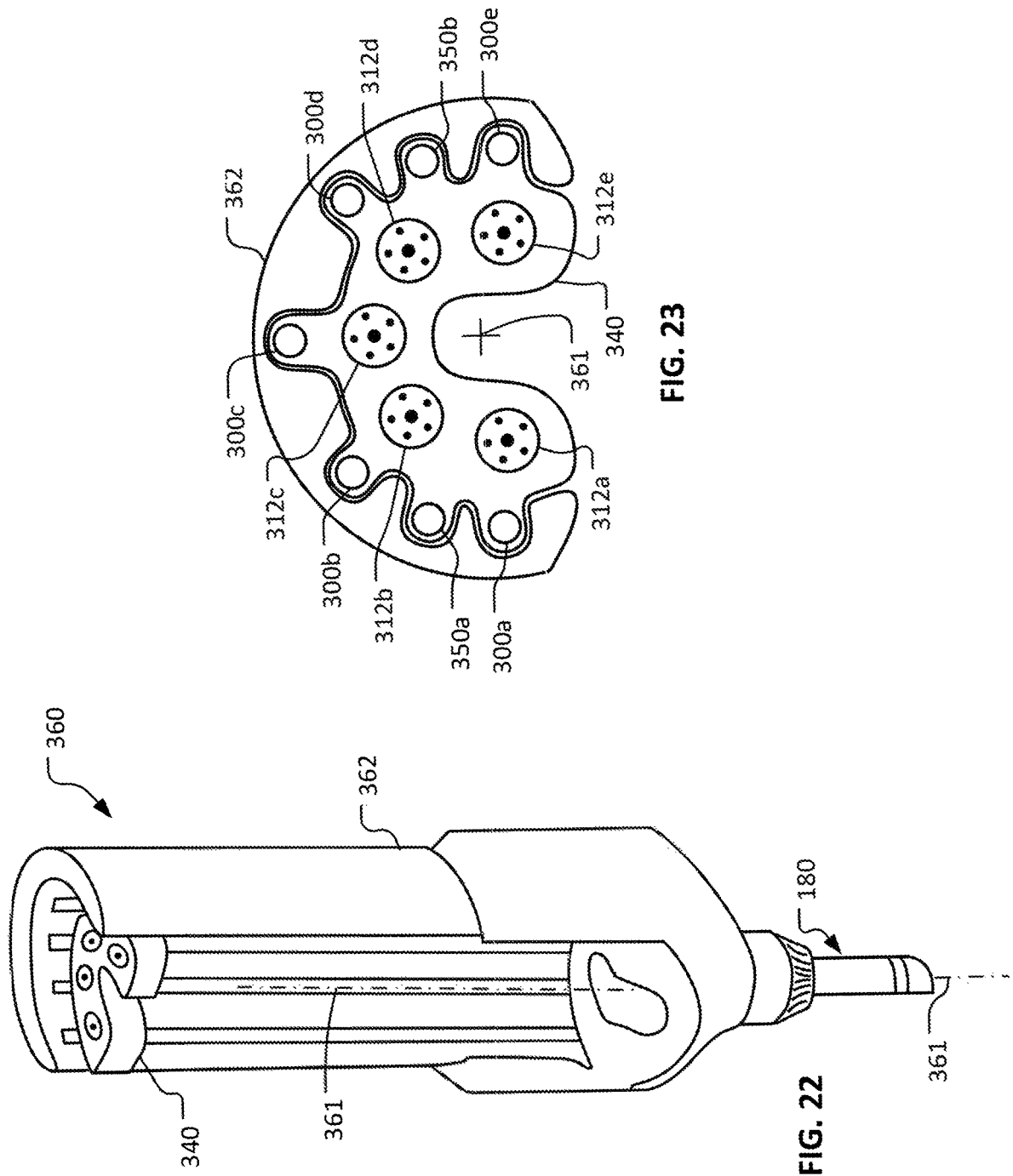

SURGICAL INSTRUMENT ACTUATION MECHANISMS

CROSS-REFERENCE TO RELATED APPLICATIONS

This application is a U.S. National Stage Application under 35 U.S.C. § 371 and claims the benefit of International Application Serial No. PCT/US2019/024569, filed on Mar. 28, 2019, which claims priority to U.S. Provisional Patent Application No. 62/650,115, filed on Mar. 29, 2018, the entire contents of both of which are hereby incorporated by reference.

COPYRIGHT NOTICE

A portion of the disclosure of this patent document contains material which is subject to copyright protection. The copyright owner has no objection to the facsimile reproduction by any-one of the patent document or the patent disclosure, as it appears in the Patent and Trademark Office patent file or records, but otherwise reserves all copyright rights whatsoever.

TECHNICAL FIELD

This disclosure relates to systems and methods that can be used in various contexts such as, but not limited to, minimally invasive computer-assisted tele-operated surgery using robotic technology. For example, the disclosure relates to instruments and mechanisms for actuating and controlling the motions of such instruments. The instruments and actuator mechanisms may be used in medical operations and non-medical operations.

BACKGROUND

Robotic systems and computer-assisted devices often include robot or movable arms to manipulate instruments for performing a task at a work site and at least one robot or movable arm for supporting an image capturing device which captures images of the work site. A robot arm comprises a plurality of links coupled together by one or more actively controlled joints. In many embodiments, a plurality of actively controlled joints may be provided. The robot arm may also include one or more passive joints, which are not actively controlled, but comply with movement of an actively controlled joint. Such active and passive joints may be revolute or prismatic joints. The configuration of the robot arm may then be determined by the positions of the joints and knowledge of the structure and coupling of the links.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a stereoscopic and/or three-dimensional image of the surgical site on a suitable viewer or display, the surgeon performs the surgical procedures on the patient by manipulating master control input devices, which in turn control the motion of surgical instruments. The surgical instruments can be configured to be inserted through small, minimally invasive surgical apertures to treat tissues at surgical sites within the patient, often lessening the trauma associated with accessing for open surgery. These robotic systems can move the working ends or end-effectors of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

SUMMARY

The following summary introduces certain aspects of the inventive subject matter in order to provide a basic understanding. This summary is not an extensive overview of the inventive subject matter, and it is not intended to identify key or critical elements or to delineate the scope of the inventive subject matter. Although this summary contains information that is relevant to various aspects and embodiments of the inventive subject matter, its sole purpose is to present some aspects and embodiments in a general form as a prelude to the more detailed description below.

This disclosure provides systems and methods for computer-assisted medical operations and non-medical operations. For example, the disclosure provides systems and methods for assisting minimally invasive computer-assisted tele-operated surgery (also referred to herein as "robotic surgery" and "computer-assisted surgery"). For example, the disclosure provides instruments, and systems and mechanisms for actuating and controlling motions of instruments in various medical operations and non-medical operations.

In one aspect, this disclosure describes surgical instrument actuation mechanism. Such a surgical instrument actuation mechanism includes a spline shaft and a collar slidably mated with the spline shaft. The collar is configured to transmit driving force from the spline shaft to a surgical instrument drive input in response to rotation of the spline shaft.

Such a surgical instrument actuation mechanism may optionally include one or more of the following features. The surgical instrument actuation mechanism may also include a carriage that translates in relation to the spline shaft. The collar may be coupled to the carriage. At least a portion of the collar may rotate relative to the carriage in response to rotation of the spline shaft. The carriage may be configured to releasably couple with a surgical instrument. The surgical instrument actuation mechanism may also include a leadscrew threadedly coupled to the carriage. The surgical instrument actuation mechanism may also include a first motor engaged to rotatably drive the spline shaft, and may have a second motor engaged to rotatably drive the leadscrew. The spline shaft may be an elongate spur gear that meshes with the surgical instrument drive input. The surgical instrument actuation mechanism may also include a lead-in member adjacent to an end of the elongate spur gear and having a tapered shape. At least a portion of the tapered shape may correspond to a cross-sectional shape of the elongate spur gear. An end of the elongate spur gear may be diametrically tapered. The collar may comprise a bevel gear that meshes with the surgical instrument drive input. The surgical instrument actuation mechanism may also include a roll drive motor. The roll drive motor may drive rotation of an entirety of the surgical instrument actuation mechanism about its longitudinal axis.

In another aspect, this disclosure is directed to a surgical instrument actuation mechanism that includes a spline shaft, a collar slidably mated with the spline shaft, and a bevel gear coupled to the collar. The bevel gear is positioned to engage with a surgical instrument drive input and configured to transmit torque from the spline shaft to the surgical instrument drive input in response to rotation of the spline shaft.

Such a surgical instrument actuation mechanism may optionally include one or more of the following features. The spline shaft may be a first spline shaft, the collar may be a first collar, the bevel gear may be a first bevel gear, the surgical instrument drive input may be a first surgical instrument drive input, and the surgical instrument actuation mechanism may also include: a second spline shaft; a second collar slidably mated with the second spline shaft; and a second bevel gear coupled to the second collar. The second bevel gear may be positioned to engage with a second surgical instrument drive input and configured to transmit torque from the second spline shaft to the second surgical instrument drive input in response to rotation of the second spline shaft. The collar may include either a ball spline bearing or a bushing that slides along the spline shaft. The surgical instrument actuation mechanism may also include a carriage. The spline shaft may extend through the carriage. The carriage may be translatable along the spline shaft. The surgical instrument actuation mechanism may also include a leadscrew threadedly coupled to the carriage such that rotation of the leadscrew drives translation of the carriage along the spline shaft. The surgical instrument actuation mechanism may also include a first motor engaged to rotatably drive the spline shaft, and a second motor engaged to rotatably drive the leadscrew. At least a portion of the collar may be rotatable in relation to the carriage. At least a portion of the collar may be fixed in relation to the carriage. The carriage may include a surgical instrument mount. The surgical instrument actuation mechanism may also include a roll drive motor. The roll drive motor may drive rotation of an entirety of the surgical instrument actuation mechanism about its longitudinal axis.

In another aspect, this disclosure is directed to a surgical instrument actuation mechanism that includes a spline shaft positioned to mesh with a spur gear drive input of a surgical instrument, and a collar slidably mated with the spline shaft. The spline shaft may transmit torque to the spur gear drive input of the surgical instrument in response to rotation of the spline shaft.

Such a surgical instrument actuation mechanism may optionally include one or more of the following features. The spline shaft's outer periphery may include gear teeth at multiple cross-sections along the spline shaft. The spline shaft may include a spur gear with an elongate face width. The collar may include an internal gear that meshes with the spur gear. The surgical instrument actuation mechanism may also include a lead-in member adjacent to an end of the spline shaft and having a tapered shape. At least a portion of the tapered shape may correspond to a cross-sectional shape of the spline shaft. An end of the spline shaft may be diametrically tapered. The spline shaft may be a first spline shaft, the collar may be a first collar, the spur gear drive input of the surgical instrument may be a first spur gear drive input of the surgical instrument, and the surgical instrument actuation mechanism may also include: a second spline shaft positioned to mesh with a second spur gear drive input of the surgical instrument; and a second collar slidably mated with the second spline shaft. The second spline shaft may transmit torque to the second spur gear drive input of the surgical instrument in response to rotation of the second spline shaft. The surgical instrument actuation mechanism may also include a carriage. The spline shaft may extend through the carriage. The carriage may be translatable along the spline shaft. The surgical instrument actuation mechanism may also include a leadscrew threadedly coupled to the carriage such that rotation of the leadscrew drives translation of the carriage along the spline shaft. The surgical instrument actuation mechanism may also include a first motor engaged to rotatably drive the spline shaft, and a second motor engaged to rotatably drive the leadscrew. At least a portion of the collar may be rotatable in relation to the carriage. At least a portion of the collar may be fixed in relation to the carriage. The carriage may comprise a surgical instrument mount. The surgical instrument actuation mechanism may also include a roll drive motor. The roll drive motor may drive rotation of an entirety of the surgical instrument actuation mechanism about its longitudinal axis.

In another aspect, this disclosure is directed to a surgical instrument for a telesurgical system. Such a surgical instrument includes a proximal end portion; an instrument shaft extending from the proximal end portion and having a distal end portion opposite from the proximal end portion; an end effector mounted to the distal end portion, the end effector having a first degree of freedom whereby the end effector is movable relative to the instrument shaft and a second degree of freedom whereby the end effector is movable relative to the instrument shaft; a first tensioning member coupled to the end effector and extending along the instrument shaft, the first tensioning member terminating at a first instrument drive input, the first instrument drive input movably coupled to the proximal end portion; and a second tensioning member coupled to the end effector and extending along the instrument shaft, the second tensioning member terminating at a second instrument drive input, the second instrument drive input movably coupled to the proximal end portion. The first instrument drive input is a first bevel gear and the second instrument drive input is a second bevel gear.

Such a surgical instrument may optionally include one or more of the following features. The first bevel gear is at a first distance away from the end effector, the second bevel gear is at a second distance away from the end effector, and the first distance may be different than the second distance. The instrument shaft defines a longitudinal axis, the first bevel gear is at a first distance away from the end effector along the longitudinal axis, the second bevel gear is at a second distance away from the end effector along the longitudinal axis, and the first distance may be different than the second distance. Rotation of the first bevel gear may move the end effector along the first degree of freedom. Rotation of the second bevel gear may move the end effector along the second degree of freedom. The first bevel gear may be coupled to a first capstan. The first tensioning member may include a first cable that is wrapped around the first capstan. The second bevel gear may be coupled to a second capstan. The second tensioning member may include a second cable that is wrapped around the second capstan. The surgical instrument may also include a third tensioning member coupled to the end effector and extending along the instrument shaft. The third tensioning member may be terminated at a third instrument drive input. The third instrument drive input may be movably coupled to the proximal end portion. The third instrument drive input may be a third bevel gear. The surgical instrument may include a latch mechanism movably coupled to the proximal end portion and configured for releasably latching the surgical instrument to an instrument actuator of the telesurgical system.

In another aspect, this disclosure is directed to a surgical instrument for a telesurgical system. The surgical instrument includes: a proximal end portion; an instrument shaft extending from the proximal end portion along a longitudinal axis and having a distal end portion opposite from the proximal end portion; an end effector mounted to the distal end portion, the end effector having a first degree of freedom whereby the end effector is movable relative to the instrument shaft and a second degree of freedom whereby the end effector is movable relative to the instrument shaft; a first tensioning member coupled to the end effector and extending along the instrument shaft, the first tensioning member terminating at a first instrument drive input, the first instrument drive input movably coupled to the proximal end portion; and a second tensioning member coupled to the end effector and extending along the instrument shaft, the second tensioning member terminating at a second instrument drive input, the second instrument drive input movably coupled to the proximal end portion. The first instrument drive input is a first spur gear and the second instrument drive input is a second spur gear.

Such a surgical instrument may optionally include one or more of the following features. The first and second spur gears include teeth and valleys defined between adjacent pairs of teeth, and the teeth and the valleys may extend parallel to the longitudinal axis of the instrument shaft. Rotation of the first spur gear may move the end effector along the first degree of freedom. Rotation of the second spur gear may move the end effector along the second degree of freedom. The first spur gear may be coupled to a first capstan. The first tensioning member may include a first cable that is wrapped around the first capstan. The second spur gear may be coupled to a second capstan. The second tensioning member may include a second cable that is wrapped around the second capstan. The surgical instrument may also include a first spring that is coupled to the first capstan and exerting spring force to tension the first cable. The surgical instrument may also include a second spring that is coupled to the second capstan and exerting spring force to tension the second cable.

In another aspect, this disclosure is directed to a surgical instrument for a telesurgical system. The surgical instrument includes: a proximal end portion; an instrument shaft extending from the proximal end portion and having a distal end portion opposite from the proximal end portion; an end effector mounted to the distal end portion, the end effector having at least a first degree of freedom whereby the end effector is movable relative to the instrument shaft; a first tensioning member coupled to the end effector and extending along the instrument shaft, the first tensioning member terminating at a first instrument drive input, the first instrument drive input slidably coupled to the proximal end portion; and a second tensioning member coupled to the end effector and extending along the instrument shaft. The second tensioning member terminates at a second instrument drive input. The second instrument drive input is slidably coupled to the proximal end portion. Moving the first instrument drive input proximally moves the second instrument drive input distally and moves the end effector in a first manner relative to the instrument shaft. The first manner including movement facilitated by the first degree of freedom. Moving the second instrument drive input proximally moves the first instrument drive input distally and moves the end effector in a second manner relative to the instrument shaft. The second manner may be facilitated by the first degree of freedom and oppose the first manner.

Such a surgical instrument may optionally include one or more of the following features. The surgical instrument may also include one or more pre-load tensioning members that tension the first tensioning member and the second tensioning member. The one or more pre-load tensioning members each include a spring. The end effector may move in the first manner relative to the instrument shaft when a first tensile force of the first tensioning member is greater than a second tensile force of the second tensioning member. The end effector may move in the second manner that is in opposition to the first manner when the second tensile force is greater than the first tensile force. The end effector may have at least a second degree of freedom. The surgical instrument may also include: a third tensioning member coupled to the end effector and extending along the instrument shaft, the third tensioning member terminating at a third instrument drive input, the third instrument drive input slidably coupled to the proximal end portion; and a fourth tensioning member coupled to the end effector and extending along the instrument shaft, the fourth tensioning member terminating at a fourth instrument drive input, the fourth instrument drive input slidably coupled to the proximal end portion. Moving the third instrument drive input proximally moves the fourth instrument drive input distally and moves the end effector in a third manner relative to the instrument shaft. The third manner comprising movement facilitated by the second degree of freedom. Moving the fourth instrument drive input proximally may move the third instrument drive input distally and move the end effector in a fourth manner relative to the instrument shaft. The fourth manner may be facilitated by the second degree of freedom and oppose the third manner.

In another aspect, this disclosure is directed to a surgical instrument actuation mechanism. Such a surgical instrument actuation mechanism includes: a pinion gear axle; a pinion gear on the pinion gear axle; a worm gear coupled to the pinion gear; a first spline shaft; a first collar slidably mated with the first spline shaft and comprising a worm meshed with the worm gear; a second spline shaft; and a second collar slidably mated with the second spline shaft and comprising a screw threadedly coupled to the pinion gear axle.

Such a surgical instrument actuation mechanism may optionally include one or more of the following features. The first collar, the second collar, the worm, and the screw may be oriented along a longitudinal direction of the surgical instrument actuation mechanism. The pinion gear axle may be oriented in a lateral direction orthogonal to the longitudinal direction. The surgical instrument actuation mechanism may also include a first rack meshed with the pinion gear, and a second rack meshed with the pinion gear. The first rack and the second rack may translate in opposing directions in response to rotations of the pinion gear. The first rack and the second rack may each translate parallel to a longitudinal direction of the surgical instrument actuation mechanism. The first rack and the second rack may each comprise surgical instrument drive input engagement features. The surgical instrument actuation mechanism may also include a first carriage, and a first leadscrew threadedly coupled with the first carriage. The first leadscrew may extend parallel to a longitudinal direction of the surgical instrument actuation mechanism. The first carriage may translate along the longitudinal direction in response to rotations of the first leadscrew. The first carriage may include a surgical instrument mount. The surgical instrument actuation mechanism may also include a second carriage. The pinion gear axel may extend from the second carriage. The second carriage may be threadedly coupled to the screw of the second collar. The surgical instrument actuation mechanism may also include a first force sensor arranged to detect a force between the first carriage and the second carriage. The surgical instrument actuation mechanism may also include a first rack meshed with the pinion gear, and a second rack meshed with the pinion gear. The first rack and the second rack may slidably translate on slides mounted to the first carriage. The first carriage may include: a first platform member; and a second platform member fixedly coupled to the first platform member in a spaced apart arrangement. The first spline shaft, the second spline shaft, and the first leadscrew may extend through the first platform member and the second platform member. The second platform member may be fixedly coupled to the first platform member by slides on which the first rack and the second rack slidably translate. The surgical instrument actuation mechanism may also include three motors. Each motor may be engaged to rotatably drive a respective one of the first spline shaft, the second spline shaft, and the first leadscrew. The surgical instrument actuation mechanism may also include a second leadscrew threadedly coupled with the first carriage. A single leadscrew drive gear may simultaneously drives both the first leadscrew and the second leadscrew. The surgical instrument actuation mechanism may also include a roll drive motor. The roll drive motor may drive rotation of an entirety of the surgical instrument actuation mechanism about its longitudinal axis. The surgical instrument actuation mechanism may be releasably coupleable to a manipulator arm of a tele-operated surgical system. The pinion gear axle may be a first pinion gear axle. The pinion gear may be a first pinion gear. The worm gear may be a first worm gear. The worm may be a first worm. The screw may be a first screw. The surgical instrument actuation mechanism may also include: a second pinion gear axle; a second pinion gear on the second pinion gear axle; a second worm gear coupled to the second pinion gear; a third spline shaft; a third collar slidably mated with the third spline shaft and comprising a second worm meshed with the second worm gear; a fourth spline shaft; and a fourth collar slidably mated with the fourth spline shaft and comprising a second screw threadedly coupled to the second pinion gear axle.

In another aspect, this disclosure is directed to a surgical instrument actuation mechanism. Such a surgical instrument actuation mechanism includes a first spline shaft; a second spline shaft; a carriage translatable along the first and second spline shafts; and a collar slidably mated with the second spline shaft and threadedly coupled with the carriage.

Such a surgical instrument actuation mechanism may optionally include one or more of the following features. The surgical instrument actuation mechanism may also include a pinion gear axle extending from the carriage, and a pinion gear rotatably coupled to the pinion gear axle. The collar may be a second collar, the surgical instrument actuation mechanism may also include a first collar slidably mated with the first spline shaft, and the first collar may include a worm meshed with a worm gear that is coupled to the pinion gear. The first collar, the second collar, the first spline shaft, and the second spline shaft may be each oriented parallel to a longitudinal axis of the surgical instrument actuation mechanism. The pinion gear axle may be oriented in a lateral direction orthogonal to the longitudinal axis. The surgical instrument actuation mechanism may also include a first rack meshed with the pinion gear, and a second rack meshed with the pinion gear. The first rack and the second rack may be meshed with the pinion gear at diametrically opposite sides of the pinion gear. The collar, the first spline shaft, and the second spline shaft may be each oriented parallel to a longitudinal axis of the surgical instrument actuation mechanism. The pinion gear axle may be oriented in a lateral direction orthogonal to the longitudinal axis. The carriage may be a second carriage, and the surgical instrument actuation mechanism may also include a first carriage, and a first leadscrew threadedly coupled with the first carriage. The first leadscrew may extend parallel to a longitudinal axis of the surgical instrument actuation mechanism, and the first carriage may translate along the longitudinal axis in response to rotations of the first leadscrew. The first carriage may include a surgical instrument mount. The first carriage may include a first platform member, and a second platform member fixedly coupled to the first platform member in a spaced apart arrangement. The second carriage may be disposed between the first platform member and the second platform member. The surgical instrument actuation mechanism may also include a first rack meshed with the pinion gear, and a second rack meshed with the pinion gear. The second platform member may be fixedly coupled to the first platform member by slides on which the first rack and the second rack slidably translate. The surgical instrument actuation mechanism may also include three motors. Each motor may be engaged to rotatably drive a respective one of the first spline shaft, the second spline shaft, and the first leadscrew. The surgical instrument actuation mechanism may also include a second leadscrew threadedly coupled with the first carriage. A single leadscrew drive gear may simultaneously drives both the first leadscrew and the second leadscrew. The surgical instrument actuation mechanism may also include a roll drive motor. The roll drive motor may drive rotation of an entirety of the surgical instrument actuation mechanism about its longitudinal axis.

In another aspect, this disclosure is directed to a surgical instrument actuation mechanism. Such a surgical instrument actuation mechanism includes a first spline shaft; a second spline shaft; a first rack; a second rack, wherein the first rack and the second rack each comprise means for driving corresponding surgical instrument drive inputs; means for translating the first and second racks in opposite directions in response to rotation of the first spline shaft; and means for translating the first and second racks in a same direction in response to rotation of the second spline shaft.

Such a surgical instrument actuation mechanism may optionally include one or more of the following features. The means for translating the first and second racks in the opposite directions in response to rotation of the first spline shaft may include means for rotating a pinion gear meshed with the first and second racks. The means for rotating the pinion gear meshed with the first and second racks may include a worm gear coupled to the pinion gear and meshed with a worm. The means for rotating the pinion gear meshed with the first and second racks may further comprise means for rotating the worm. The surgical instrument actuation mechanism may also include a first collar slidably mated to the first spline shaft and comprising the worm. The means for rotating the worm may include the first collar and the first spline shaft. The means for translating the first and second racks in the same direction in response to rotation of the second spline shaft may comprise means for translating a pinion gear meshed with the first and second racks. The means for translating the pinion gear meshed with the first and second racks may comprise a pinion gear axle to which the pinion gear is rotatably coupled. The means for translating the first and second racks in the same direction in response to rotation of the second spline shaft may further comprise means for translating the pinion gear axle. The surgical instrument actuation mechanism may include a second collar slidably mated to the second spline shaft and threadedly coupled to the pinion gear axle. The means for translating the pinion gear axle may comprise the second collar and the second spline shaft.

In another aspect, this disclosure is directed to a surgical system that includes an instrument manipulator and a surgical instrument that includes a handle. The instrument manipulator includes an outer housing and an instrument receptacle in the outer housing. The outer housing extends around a longitudinal axis. A proximal portion of the outer housing defines a proximal outer housing boundary around the longitudinal axis. A distal portion of the outer housing defines a distal outer housing boundary. The distal portion of the outer housing has a cutout volume extending along the longitudinal axis. A radial extension of the handle of the surgical instrument is completely within the cutout volume while the surgical instrument is received in the instrument receptacle of the instrument manipulator.

Such a surgical system may optionally include one or more of the following features. The cutout volume may extend parallel to the longitudinal axis. The distal portion of the outer housing may have a D-shaped cross-section that includes a curved wall portion and a flat wall portion. The cutout volume may be defined between the flat wall portion and an extension of the curved wall portion that is radially outward of the flat wall portion. A cross-sectional shape of the curved wall portion may be an arcuate or circular segment wall portion. The cutout volume may have a D-shaped cross-sectional shape. The proximal portion of the outer housing may have a smaller outer profile that the distal portion of the outer housing. The radial extension of the handle may extend radially beyond the proximal outer housing boundary while the surgical instrument is received in the instrument receptacle of the instrument manipulator.

In another aspect, this disclosure is directed to a surgical system that includes a surgical instrument actuation mechanism comprising a housing defining an outer periphery, and a surgical instrument releasably coupleable with the surgical instrument actuation mechanism and comprising a handle. While the surgical instrument is coupled with the surgical instrument actuation mechanism, the handle is within a radius of a maximum outer periphery of the housing and extends radially outward from a radius of a minimum outer periphery of the housing.

Such a surgical system may optionally include one or more of the following features. The maximum outer periphery of the housing may be a distal portion of the housing and the minimum outer periphery of the housing may be a proximal portion of the housing. The maximum outer periphery of the housing may be a curved portion of a D-shaped cross-sectional shape. The handle may extend radially outward from a flattened wall of the D-shaped cross-sectional shape. The curved portion of the D-shaped cross-sectional shape may be arcuate.

In another aspect, this disclosure is directed to a surgical system that includes a surgical instrument actuation mechanism and a surgical instrument. The surgical instrument actuation mechanism includes a housing, and a carriage disposed within the housing and configured to translate between a proximal end of the housing and a distal end of the housing. The surgical instrument is releasably coupleable with the carriage. The surgical instrument includes a handle extending radially away from a longitudinal axis of the housing. While the surgical instrument is coupled with the carriage: (i) the handle extends radially outward farther than the housing while the carriage is at the proximal end of the housing and (ii) the housing extends radially outward farther than the handle while the carriage is at the distal end of the housing.

Such a surgical system may optionally include one or more of the following features. The distal end of the housing may have a D-shaped cross-sectional shape. The D-shaped cross-sectional shape may include an arcuate portion and a flat portion. The handle may extend radially outward farther than the flat portion. The arcuate portion housing may extend radially outward farther than the handle. A cutout volume may be defined between the flat portion and an extension of the arcuate portion that is radially outward of the flat portion. The cutout volume may have a D-shaped cross-sectional shape and extends parallel to the longitudinal axis of the housing. In some embodiments, the handle does not extend radially beyond the cutout volume. The surgical instrument may be releasably coupleable with the carriage using a spring-loaded latch mechanism.

Some or all of the embodiments described herein may provide one or more of the following advantages. First, the instrument actuation systems and mechanisms described herein are advantageously structured to be compact and to have a relatively low mass and inertia. In addition, the mass distribution is substantially constant such that the inertia is substantially constant, and therefore predictable and well-suited to modeling.

Second, in some embodiments the instrument actuation systems and mechanisms described herein are advantageously structured to interface with a surgical instrument in a manner that is readily detachable. For example, in some embodiments the surgical instrument can be detached from an instrument drive system merely by actuating a latch mechanism and retracting the instrument proximally out of engagement with the drive system. Such a readily detachable interface between the surgical instrument and the instrument drive system can provide advantages such as quick instrument removal in the event of an emergency, and user convenience during general change-outs of one surgical instrument for another.

Third, in some embodiments the instrument actuation systems and mechanisms described herein are designed with spline drive shafts and other mechanical transmission components that can advantageously reduce the number of parts required for the instrument actuation systems and mechanisms. Such simplified designs can typically provide high reliability and facilitate ease of maintenance.

The details of one or more embodiments are set forth in the accompanying drawings and the description below. Other features, objects, and advantages will be apparent from the description and drawings, and from the claims.

BRIEF DESCRIPTION OF THE DRAWINGS

FIG. 6 is a perspective view of an example instrument in accordance with some embodiments.

FIG. 7 is a perspective view of an example manipulator arm, instrument actuator, and the instrument of FIG. 6.

FIG. 8 is an exploded perspective view of an example spline shaft and collar in accordance with some embodiments.

FIG. 9 is a perspective view of the spline shaft and collar of FIG. 8 in a coupled arrangement.

FIG. 18 is a perspective view of the spline shaft of FIG. 8 coupled with an example collar comprising a spur gear.

FIG. 19 is a perspective view of the spline shaft of FIG. 8 coupled with an example collar comprising a bevel gear.

FIG. 22 is a perspective view of an example instrument actuator that includes spline shaft and collar mechanisms.

FIG. 23 is a partial top view of the instrument actuator of FIG. 22.

Like reference symbols in the various drawings indicate like elements.

DETAILED DESCRIPTION

Figure 1:
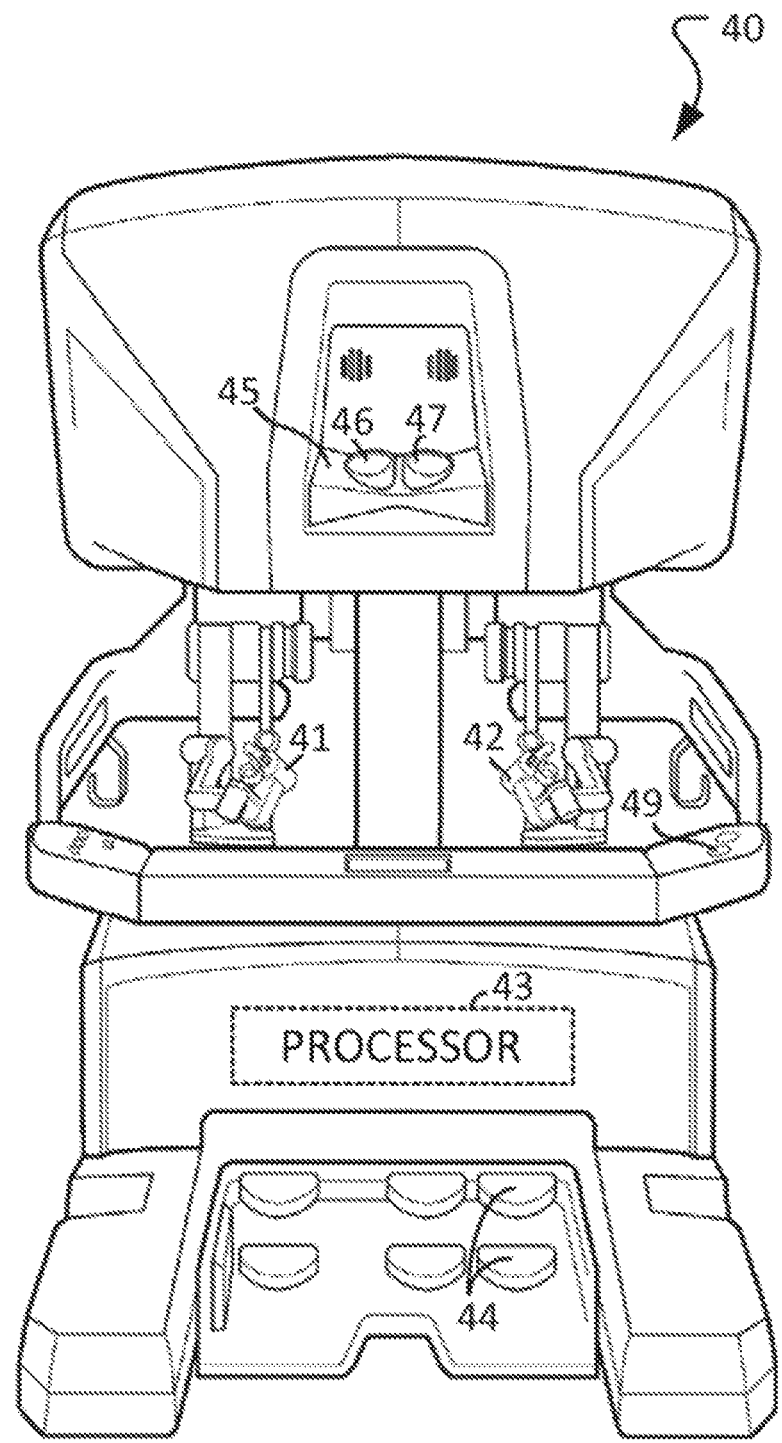
FIG. 1 is a front view of an example surgeon console of a computer-assisted tele-operated surgery system or robotic surgery system.

This description and the accompanying drawings that illustrate inventive aspects, embodiments, implementations, or applications should not be taken as limiting—the claims define the protected invention. Various mechanical, compositional, structural, electrical, and operational changes may be made without departing from the spirit and scope of this description and the claims. In some instances, well-known circuits, structures, or techniques have not been shown or described in detail in order not to obscure the invention. Like numbers in two or more figures represent the same or similar elements.

Further, specific words chosen to describe one or more embodiments and optional elements or features are not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., translational placements) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (e.g., rotated 90 degrees or at other orientations) and the spatially relative descriptors used herein interpreted accordingly. Likewise, descriptions of movement along (translation) and around (rotation) various axes includes various special device positions and orientations. The combination of a body's position and orientation define the body's pose.

Similarly, geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. The words "including" or "having" mean including but not limited to.

It should be understood that although this description is made to be sufficiently clear, concise, and exact, scrupulous and exhaustive linguistic precision is not always possible or desirable, since the description should be kept to a reasonable length and skilled readers will understand background and associated technology. For example, considering a video signal, a skilled reader will understand that an oscilloscope described as displaying the signal does not display the signal itself but a representation of the signal, and that a video monitor described as displaying the signal does not display the signal itself but video information the signal carries.

In addition, the singular forms "a", "an", and "the" are intended to include the plural forms as well, unless the context indicates otherwise. And, the terms "comprises", "includes", "has", and the like specify the presence of stated features, steps, operations, elements, and/or components but do not preclude the presence or addition of one or more other features, steps, operations, elements, components, and/or groups. And, the or each of the one or more individual listed items should be considered optional unless otherwise stated, so that various combinations of items are described without an exhaustive list of each possible combination. The auxiliary verb may likewise implies that a feature, step, operation, element, or component is optional.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Elements described as coupled may be electrically or mechanically directly coupled, or they may be indirectly coupled via one or more intermediate components.

The term "flexible" in association with a part, such as a mechanical structure, component, or component assembly, should be broadly construed. In essence, the term means the part can be repeatedly bent and restored to an original shape without harm to the part. Many "rigid" objects have a slight inherent resilient "bendiness" due to material properties, although such objects are not considered "flexible" as the term is used herein. A flexible part may have infinite degrees of freedom (DOF's). Examples of such parts include closed, bendable tubes (made from, e.g., NITINOL, polymer, soft rubber, and the like), helical coil springs, etc. that can be bent into various simple or compound curves, often without significant cross-sectional deformation. Other flexible parts may approximate such an infinite-DOF part by using a series of closely spaced components that are similar to a snake-like arrangement of serial "vertebrae." In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible part may serve as, and be modeled as, a single mechanical constraint (joint) that provides one or more DOF's between two links in a kinematic chain, even though the flexible part itself may be a kinematic chain made of several coupled links. Knowledgeable persons will understand that a part's flexibility may be expressed in terms of its stiffness.

Unless otherwise stated in this description, a flexible part, such as a mechanical structure, component, or component assembly, may be either actively or passively flexible. An actively flexible part may be bent by using forces inherently associated with the part itself. For example, one or more tendons may be routed lengthwise along the part and offset from the part's longitudinal axis, so that tension on the one or more tendons causes the part or a portion of the part to bend. Other ways of actively bending an actively flexible part include, without limitation, the use of pneumatic or hydraulic power, gears, electroactive polymer (more generally, "artificial muscle"), and the like. A passively flexible part is bent by using a force external to the part (e.g., an applied mechanical or electromagnetic force). A passively flexible part may remain in its bent shape until bent again, or it may have an inherent characteristic that tends to restore the part to an original shape. An example of a passively flexible part with inherent stiffness is a plastic rod or a resilient rubber tube. An actively flexible part, when not actuated by its inherently associated forces, may be passively flexible. A single part may be made of one or more actively and passively flexible parts in series.

Aspects of the invention may be described in terms of an implementation using a da Vinci® Surgical System, commercialized by Intuitive Surgical, Inc. of Sunnyvale, California Examples of such surgical systems are the da Vinci® Xi™ Surgical System (Model IS4000) and the da Vinci® Si™ HD™ Surgical System (Model IS3000). Knowledgeable persons will understand, however, that inventive aspects disclosed herein may be embodied and implemented in various ways, including computer-assisted, non-computer-assisted, and hybrid combinations of manual and computer-assisted embodiments and implementations. Implementations on da Vinci® Surgical Systems (e.g., the Model IS4000, the Model IS3000, the Model IS2000, the Model IS1200) are merely exemplary and are not to be considered as limiting the scope of the inventive aspects disclosed herein. As applicable, inventive aspects may be embodied and implemented in both relatively smaller, hand-held, hand-operated devices and relatively larger systems that have additional mechanical support.

It should be understood that the diminutive scale of the disclosed structures and mechanisms creates unique mechanical conditions and difficulties with the construction of these structures and mechanisms that are unlike those found in similar structures and mechanisms constructed at a larger scale, because forces and strengths of materials do not scale at the same rate as the size of the mechanisms. For example, a surgical instrument having an 8 mm shaft diameter cannot simply be scaled down to a 5 mm shaft diameter due to mechanical, material property, and manufacturing considerations. Likewise, a 5 mm shaft diameter device cannot simply be scaled down to a 3 mm shaft diameter device. Significant mechanical concerns exist as physical dimensions are reduced.

A computer is a machine that follows programmed instructions to perform mathematical or logical functions on input information to produce processed output information. A computer includes a logic unit that performs the mathematical or logical functions, and memory that stores the programmed instructions, the input information, and the output information. The term "computer" and similar terms, such as "processor" or "controller", encompasses both single-location and distributed implementations.

This disclosure provides improved surgical and robotic devices, systems, and methods. The inventive concepts are particularly advantageous for use with surgical robotic systems in which a plurality of surgical tools or instruments will be mounted on and moved by an associated plurality of robotic manipulators during a surgical procedure. The robotic systems will often, but not exclusively, comprise tele-robotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. "Linkage" is used in this application to indicate a single link, and to indicate a system comprising multiple links (and one or more joints), as applicable. The large number of degrees of freedom may also allow a processor to position the manipulators to inhibit interference or collisions between these moving structures, and the like.

The manipulator assemblies or systems described herein will often include a manipulator and a tool mounted thereon (the tool often comprising a therapeutic, diagnostic, or imaging instrument in surgical versions), although the term "manipulator system" will also encompass the manipulator without the tool mounted thereon. The term "tool" encompasses both general or industrial tools and specialized surgical instruments, with these later structures often including an end effector that is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base, or be attached to a structural element such as an operating table, that can be stationary in space during at least a portion of a surgical procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both.

When used for minimally invasive robotic surgery, movement of the manipulator assembly may be controlled by one or more processors (or simply "a processor") of the system so that a shaft or intermediate portion of the tool or instrument is constrained to a safe motion through a minimally invasive surgical access site or other aperture. Such motion may include, for example, axial insertion of the shaft through the aperture site, rotation of the shaft about its axis, and pivotal motion of the shaft about a pivot point adjacent the access site, but will often preclude excessive lateral motion of the shaft which might otherwise tear the tissues adjacent the aperture or enlarge the access site inadvertently. Some or all of such constraint on the manipulator motion at the access site may be imposed using mechanical manipulator joint linkages that inhibit improper motions, or may in part or in full be imposed using robotic data processing and control techniques. Hence, such minimally invasive aperture-constrained motion of the manipulator assembly may, in some embodiments, employ between zero and four degrees of freedom of the manipulator assembly (insertion, roll, pitch, and yaw).

Many of the exemplary manipulator assemblies described herein will have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly. It should be noted that any degree of freedom that is actively position-controlled could potentially be controlled using force control, or impedance control, or admittance control, or any combination of the forgoing.

Figure 2:
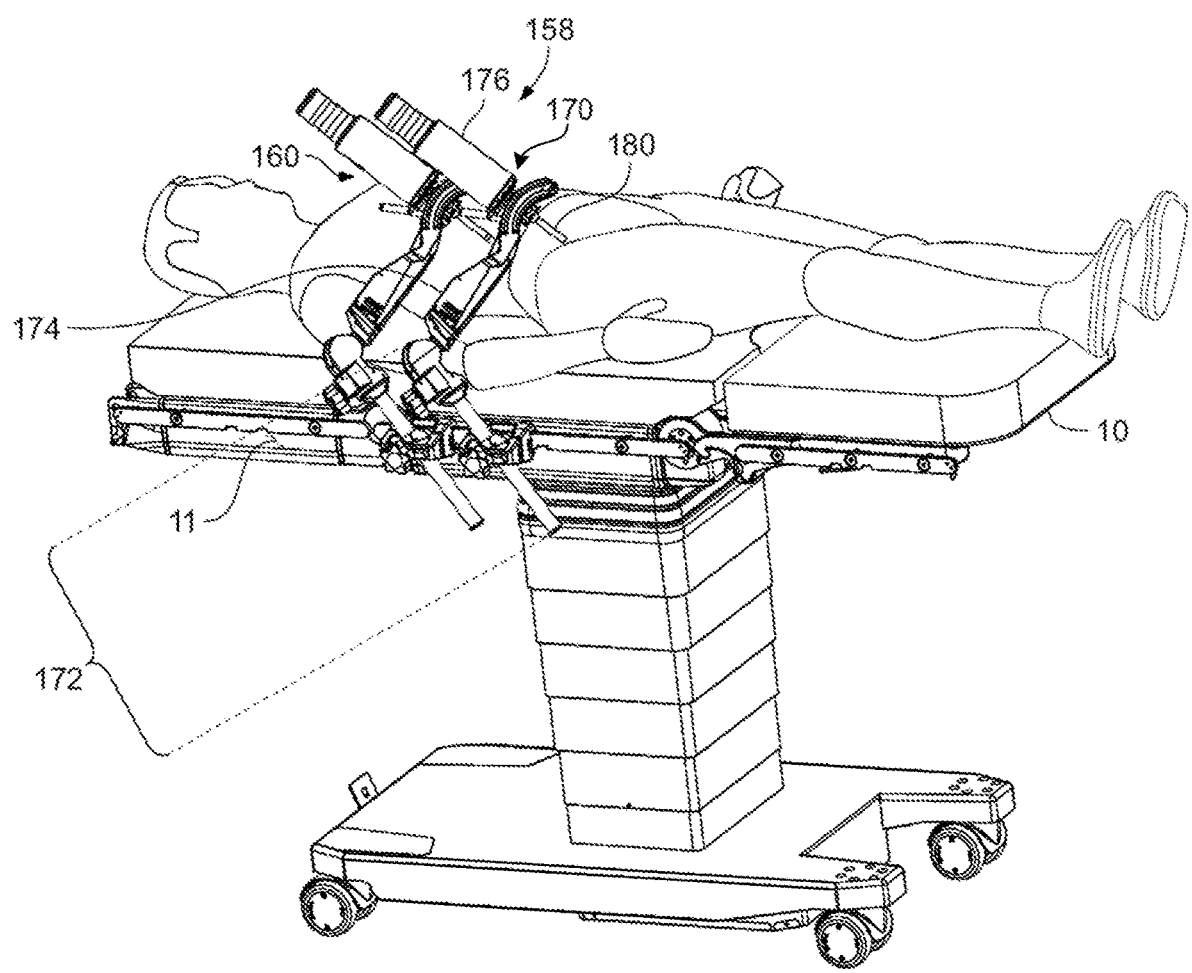
FIG. 2 is a perspective view of an example operating table on which is mounted patient-side manipulator systems and surgical instruments for computer-assisted tele-operated surgery or robotic surgery system.

Referring to FIGS. 1 and 2, computer-assisted systems using robotic technology (such as the depicted computer-assisted minimally invasive surgery system) can include a user control system (such as surgeon console 40), one or more manipulators (such as manipulator systems 160 and 170), and one or more instruments (not visible) that are used to perform tasks. In the non-limiting depicted surgical implementation, the manipulator systems 160 and 170 are mounted to an operating table 10 by adjustable support structures 172. In some implementations, manipulators are mounted to a base that can rest on a floor. Alternatively, manipulators can be attached to other stable structures such as framework, a ceiling, and the like.

In the depicted non-limiting surgical context, robotically manipulatable surgical instruments can be inserted through small, minimally invasive surgical apertures to treat tissues at surgical sites within the patient, avoiding the trauma associated with accessing for open surgery. These robotic systems can move the working ends of the surgical instruments with sufficient dexterity to perform quite intricate surgical tasks, often by pivoting shafts of the instruments at the minimally invasive aperture, sliding of the shaft axially through the aperture, rotating of the shaft within the aperture, and/or the like.

In the depicted embodiment, the surgeon console 40 includes a stereo vision display 45 so that the user may view the surgical work site in stereo vision from images captured by the stereoscopic camera of the patient-side system 158. Left and right eyepieces, 46 and 47, are provided in the stereo vision display 45 so that the user may view left and right display screens inside the display 45 respectively with the user's left and right eyes. While viewing typically an image of the surgical site on a suitable viewer or display, the surgeon performs the surgical procedures on the patient by manipulating master control input devices, which in turn control, using the processor(s) of the surgery system, the motion of robotic instruments.

The surgeon console 40 also includes left and right input devices 41, 42 that the user may grasp respectively with his/her left and right hands to manipulate devices (e.g., surgical instruments) being held by the manipulator systems 160 and 170 in preferably six degrees-of-freedom ("DOF"). Foot pedals 44 with toe and heel controls are provided on the surgeon console 40 so the user may control movement and/or actuation of devices associated with the foot pedals.

A processor 43 is provided in the surgeon console 40 for control and other purposes. The processor 43 performs various functions in the computer-assisted minimally invasive surgery system. One function performed by processor 43 is to translate and transfer the mechanical motion of input devices 41, 42 to actuate their respective joints in their associated manipulator systems 160 and 170 so that the surgeon can effectively manipulate devices, such as the surgical instruments. Another function of the processor 43 is to implement the methods, cross-coupling control logic, and controllers described herein.

Although a surgeon console 40 is described in the example above, it is to be appreciated that the operator console may be a console not designed with the surgeon as the primary user. For example, the operator console may be designed for another member of the surgical team (anesthesiologist, assistant, etc.) as the primary user, for use by the surgeon with other member(s) of the surgical team at the same or different times, or for general use by any member of the surgical team. Also, in other embodiments, the operator console may be designed for non-surgical medical uses, or for non-medical uses.

Although described as a processor, it is to be appreciated that the processor 43 (and other "processors" described herein) may be implemented by any combination of hardware, software and firmware. Also, its functions as described herein may be performed by one unit or divided up among a number of subunits, each of which may be implemented in turn by any combination of hardware, software and firmware. Further, although being shown as part of or being physically adjacent to the surgeon console 40, the processor 43 may also be distributed as subunits throughout the computer-assisted systems using robotic technology.

The processor 43 (and the processors of the other surgery systems described herein) can execute machine-readable instructions from non-transitory machine-readable media that activate the processor 43 to perform actions corresponding to the instructions. Accordingly, it should be understood that the disclosure of computer-assisted surgery techniques and methods herein includes a concomitant disclosure of non-transitory machine-readable media comprising corresponding machine-readable instructions.

In the depicted implementation, the manipulator systems 160 and 170 include a manipulator arm and an instrument actuator. For example, the manipulator system 170 includes a manipulator arm 174 and an instrument actuator 176 (which can be a surgical instrument actuator as in the depicted example or another type of instrument for other uses). The manipulator arm 174 is attached to, and extends from, the support structure 172. The instrument actuator 176 is attached to the manipulator arm 174. The manipulator arm 174 can adjust the position of the instrument actuator 176. The instrument actuator 176 (and the manipulator arm 174) can adjust the position of a surgical instrument that is mounted thereto. Such position adjustments can be made in response to inputs made to the user control system (e.g., surgeon console 40). While the depicted implementation includes two manipulator systems 160 and 170, in some implementations one, three, four, five, six, or more than six manipulator systems are included in a single computer-assisted minimally invasive surgery system.

Figure 3:
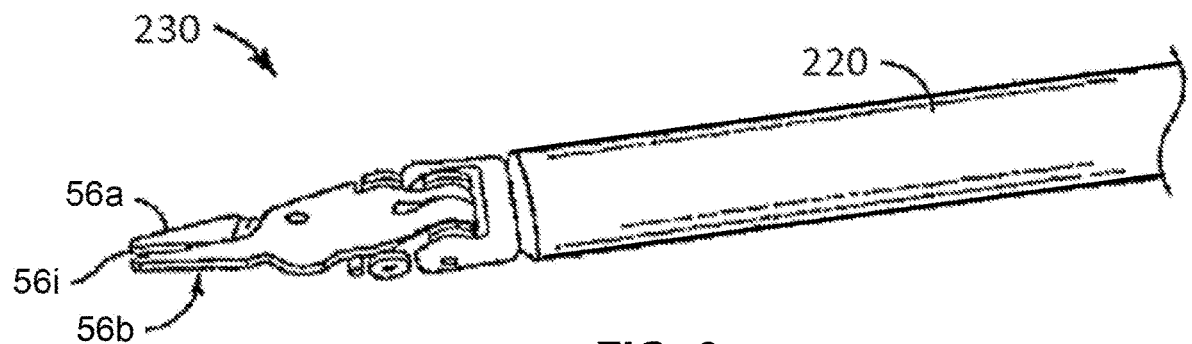
FIG. 3 is a perspective view of a distal end portion of an example surgical instrument.
Figure 4:
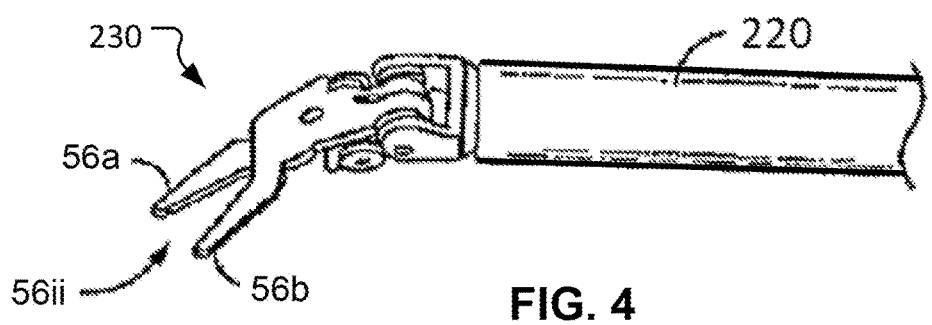
FIG. 4 is a perspective view of a distal end portion of another example surgical instrument.
Figure 5:
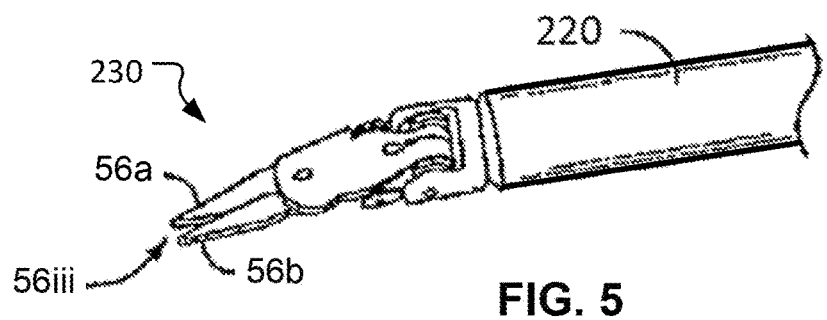
FIG. 5 is a perspective view of a distal end portion of another example surgical instrument.

Also referring to FIGS. 3-5, a variety of alternative instruments such as surgical instruments of different types and differing end effectors 230 may be used in conjunction with the instrument actuators described herein. In some cases, the instruments of at least some of the manipulators are removed and replaced during a surgical procedure. Several of these end effectors, including, for example, DeBakey Forceps 56$i$, microforceps 56$ii$, and Potts scissors 56$iii$ include first and second end effector elements 56$a$, 56$b$ which pivot relative to each other so as to define a pair of end effector jaws. Other end effectors, including scalpels, image detectors, and electrocautery probes, may have a single end effector element that may be steerable in some examples. For instruments having end effector jaws, the jaws will often be actuated by squeezing the grip members of input devices 41, 42.

The elongate shaft 220 allows the end effector 230 and the distal end portion of the shaft 220 to be inserted distally into a surgical worksite through a minimally invasive aperture (here, via cannula 180 as shown in FIG. 2), often through an abdominal wall or the like. The surgical worksite may be insufflated, and movement of the end effectors 230 within the patient will often be effected, at least in part, by pivoting of the instruments about the location at which the shaft 220 passes through the minimally invasive aperture. In other words, the manipulator systems 160 and 170 will move the surgical instrument actuators (e.g., instrument actuator 176) outside the patient so that the shaft 220 extends through a minimally invasive aperture location so as to help provide a desired movement of end effector 230. Hence, the manipulator systems 160 and 170 will often drive significant movements of the instrument actuators outside of the patient during a procedure.

Referring also to FIGS. 6 and 7, as described above, the example manipulator system 170 includes the manipulator arm 174 and the instrument actuator 176. The instrument actuator 176 is releasably attached to the manipulator arm 174, and is configured to releasably receive and engage with an instrument, such as the depicted example surgical instrument 200. For example, the instrument actuator 176 can slidingly receive the shaft 220 and can couple with a proximal end portion 210 of the instrument 200. As described further below, the proximal end portion 210 can include multiple engagement members that engage with corresponding elements of the instrument actuator 176 so as to control movements and actions of the end effector 230.

The manipulator arm 174 can adjust the position of the instrument actuator 176 (and the position of an instrument that is engaged with the instrument actuator 176). For example, the manipulator arm 174 can drive the instrument actuator 176 along an arcuate translation motion path as indicated by arrow 171. Additionally, the manipulator arm 174 can rotate so as to pivot the instrument actuator 176 as indicated by arrow 173. Such motions can be centered at a remote center of motion 181, which can be a point that is coincident with the cannula 180, for example.

In addition to the motions 171 and 173 that are driven by the manipulator arm 174, the instrument actuator 176 itself can drive various motions of an instrument that is engaged with the instrument actuator 176. For example, the instrument actuator 176 can drive motions of the surgical instrument 200 along a longitudinal axis 201 of the instrument 200 as indicated by arrow 175. Such motions along the longitudinal axis 201 of the instrument 200 (as indicated by the arrow 175) can be referred to, for example, as insertion and retraction or withdrawal motions. That is, the instrument actuator 176 can drive the instrument 200 to be inserted (moved distally) or withdrawn (moved proximally) along the longitudinal axis 201 of the instrument 200. Accordingly, the longitudinal axis 201 of the instrument 200 may also be referred to as the insertion axis. The instrument actuator 176 can also rotate in relation to the manipulator arm 174 as indicated by arrow 177. The motion indicated by arrow 177 causes the instrument 200 to turn (e.g., roll, spin, or rotate) about its longitudinal axis 201.

Novel mechanisms of instrument actuators (e.g., instrument actuator 176) that are used to drive motions of instruments (e.g., surgical instrument 200) will be described in the succeeding figures. One feature that the various instrument actuator mechanisms described herein have in common is the use of spline shafts as described further below.

Referring to FIGS. 8 and 9, in some embodiments the instrument actuators described herein can include a spline shaft as exemplified by the spline shaft 300. A collar 310 can be slidably coupled or mated with the spline shaft 300. In general, spline shafts (such as the spline shaft 300) include one or more splines which are ridges or teeth. However, almost any non-circular cross-section can be used for a spline shaft. For example, a spline shaft can have an ovular cross-sectional shape (and many other cross-sectional shapes) as described further below.

The collar 310 (which can also be described as a bushing, sleeve, nut, hub, and the like) defines an internal space that corresponds to the outer profile of the cross-sectional shape of the spline shaft 300. Accordingly, the collar 310 can slide longitudinally along the spline shaft 300 as indicated by arrow 301, but cannot rotate about the spline shaft 300. In some embodiments, the collar 310 can slide along the spline shaft 300 with the use of one or more load-carrying bearings (such as ball bearings) that run in corresponding grooves defined by the outer profile of the spline shaft 300. Such an arrangement may be referred to as ball spline bearings. Ball spline bearings allow nearly frictionless linear motion while also allowing the transmittal of torque.

In some embodiments, the collar 310 can comprise a pulley (as depicted), a sheave, a capstan, a gear, and so on. In some such embodiments, the collar 310 is thereby well-suited to transmitting torque that is input to the spline shaft 300 while being located at any position along the length of the spline shaft 300, as described further below.

Referring to FIGS. 10-15, spline shafts can have a variety of different cross-sectional shapes. It should be understood that the spline shafts shown are non-limiting examples of the different types of spline shafts that are envisioned within the scope of this disclosure. That is, many other spline shaft designs (not shown) are also possible and are envisioned within the scope of this disclosure.

Figure 10:
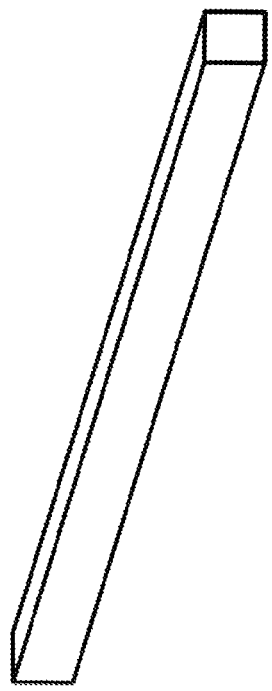
FIG. 10 is a perspective view of another example spline shaft for use in accordance with some embodiments.
Figure 11:
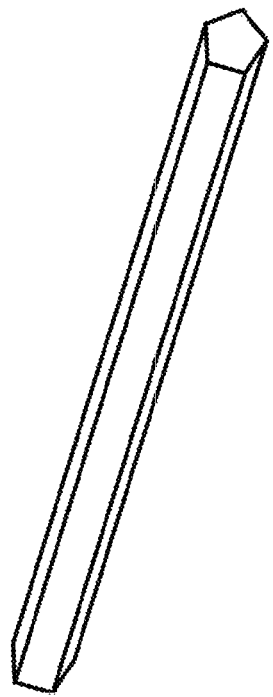
FIG. 11 is a perspective view of another example spline shaft for use in accordance with some embodiments.
Figure 12:
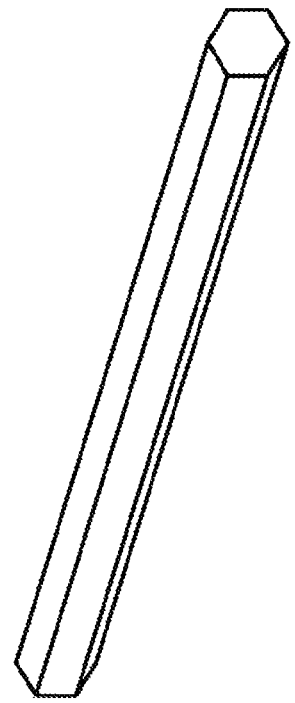
FIG. 12 is a perspective view of another example spline shaft for use in accordance with some embodiments.
Figure 13:
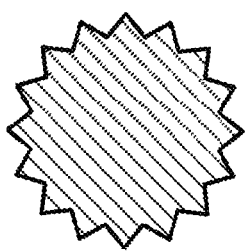
FIG. 13 is a cross-sectional view of another example spline shaft for use in accordance with some embodiments.
Figure 14:
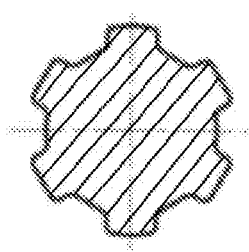
FIG. 14 is a cross-sectional view of another example spline shaft for use in accordance with some embodiments.
Figure 15:
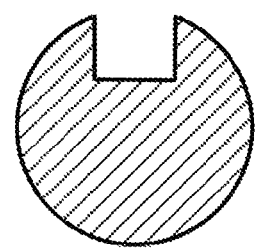
FIG. 15 is a cross-sectional view of another example spline shaft for use in accordance with some embodiments.

FIG. 10 illustrates a quadrilateral cross-sectional shape. FIG. 11 illustrates a five-sided polygonal cross-sectional shape. FIG. 12 illustrates a six-sided polygonal cross-sectional shape. FIG. 13 illustrates a multi-point star cross-sectional shape. FIG. 14 illustrates a design with six spline portions. FIG. 15 illustrates a cross-sectional shape defining a keyway. It should be understood that all other variations, modifications, extensions, combinations, and permutations of spline shafts exemplified by these designs are also included within the scope of this disclosure.

Figure 17:
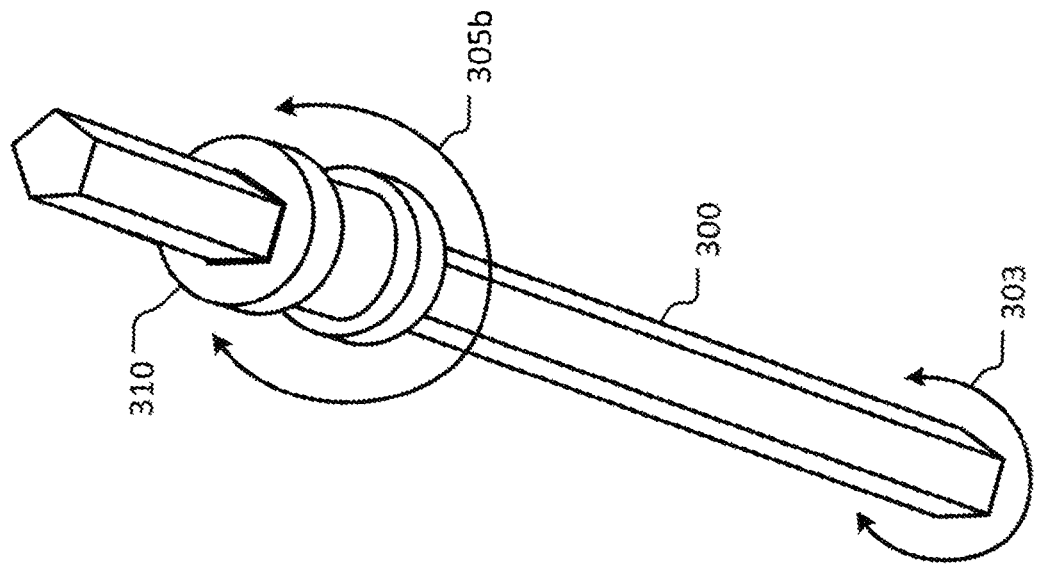
FIG. 17 is another perspective view of the spline shaft and collar of FIG. 8 in a coupled arrangement.
Figure 16:
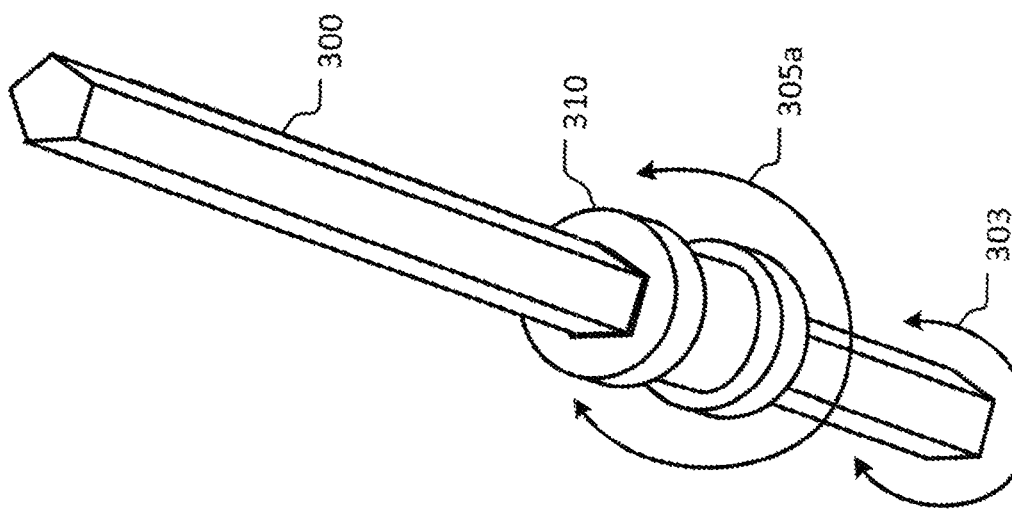
FIG. 16 is another perspective view of the spline shaft and collar of FIG. 8 in a coupled arrangement.

Referring to FIGS. 16 and 17, a spline shaft in combination with a collar can be used to transmit torque in various differing relative arrangements. For example, a torque exerted on or by the spline shaft 300 as represented by arrow 303 can be transmitted from the collar 310 while the collar 310 is in a first position (as depicted by FIG. 16; where torque being transmitted is represented by arrow 305a), and/or while the collar 310 is in a second position (as depicted by FIG. 17; where torque being transmitted is represented by arrow 305b). Accordingly, it should be understood that the collar 310 can transmit torque from the spline shaft 300 while the collar 310 is in any position along the spline shaft 300.

Referring to FIGS. 18 and 19, in some cases it can be beneficial for a collar on a spline shaft to have a shape such as, but not limited to, a gear. Various types of gears can be used as collars. For example, in some embodiments a spline shaft collar can comprise an involute spur gear collar 320 as shown in FIG. 18. In another example, a spline shaft collar can comprise a beveled gear collar 330 as shown in FIG. 18. Spline shaft collars comprising various other types of gears (e.g., helical gears, double helical gears, pinion gears, face gears, worm gears, worms, etc.) are also envisioned within the scope of this disclosure. The involute spur gear collar 320 can transmit torque represented by arrow 307 in response to a torque to the spline shaft 300 as represented by arrow 303. The beveled gear collar 330 can transmit torque represented by arrow 309 in response to a torque to the spline shaft 300 as represented by arrow 303. The gear collars 320 and 330 can slide along the spline shaft 300 as represented by arrows 301, and can transmit toque from any position along the spline shaft 300.

Figure 20:
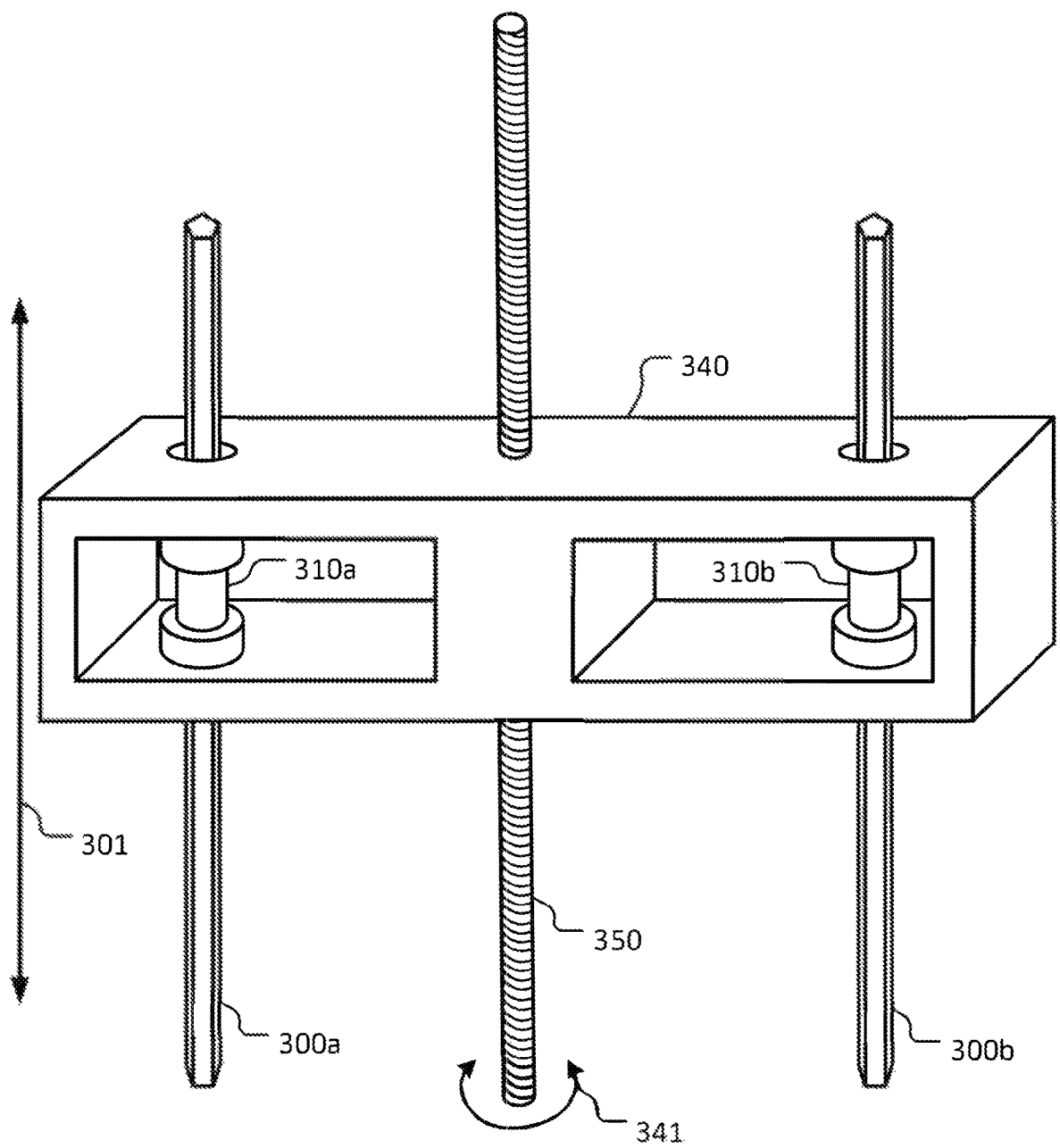
FIG. 20 schematically illustrates an example mechanism that utilizes spline shafts and collars in accordance with some embodiments.

Referring to FIG. 20, spline shafts and collars (as described above) can be advantageously incorporated with other mechanical and electro-mechanical components in various mechanisms. For example, the illustrated assembly includes two spline shafts 300a-b, two corresponding collars 310a-b, a carriage 340, and a leadscrew 350. The leadscrew 350 is threadedly coupled with the carriage 340. The spline shafts 300a-b are slidably coupled to the carriage 340. Accordingly, rotations of the leadscrew 350 as represented by arrow 341 cause the carriage 340 to translate along the spline shafts 300a-b.

In the depicted arrangement, the collars 310a-b are slidably mated to the spline shafts 330a-b while being coupled to the carriage 340 such that the collars 310a-b move linearly with the carriage 340 along the leadscrew 350 (as represented by arrow 301). At least a portion of each of the collars 310a-b is rotatable in relation to the carriage. Accordingly, a rotation of the spline shafts 330a-b cause corresponding rotations of a respective collar 310a/b in relation to the carriage 340. Said concisely, the collars 310a-b can translate along the spline shafts 300a-b and can rotate in relation to the carriage 340. Such rotary and linear movements of the collars 310a-b can occur sequentially and/or simultaneously.

Figure 21:
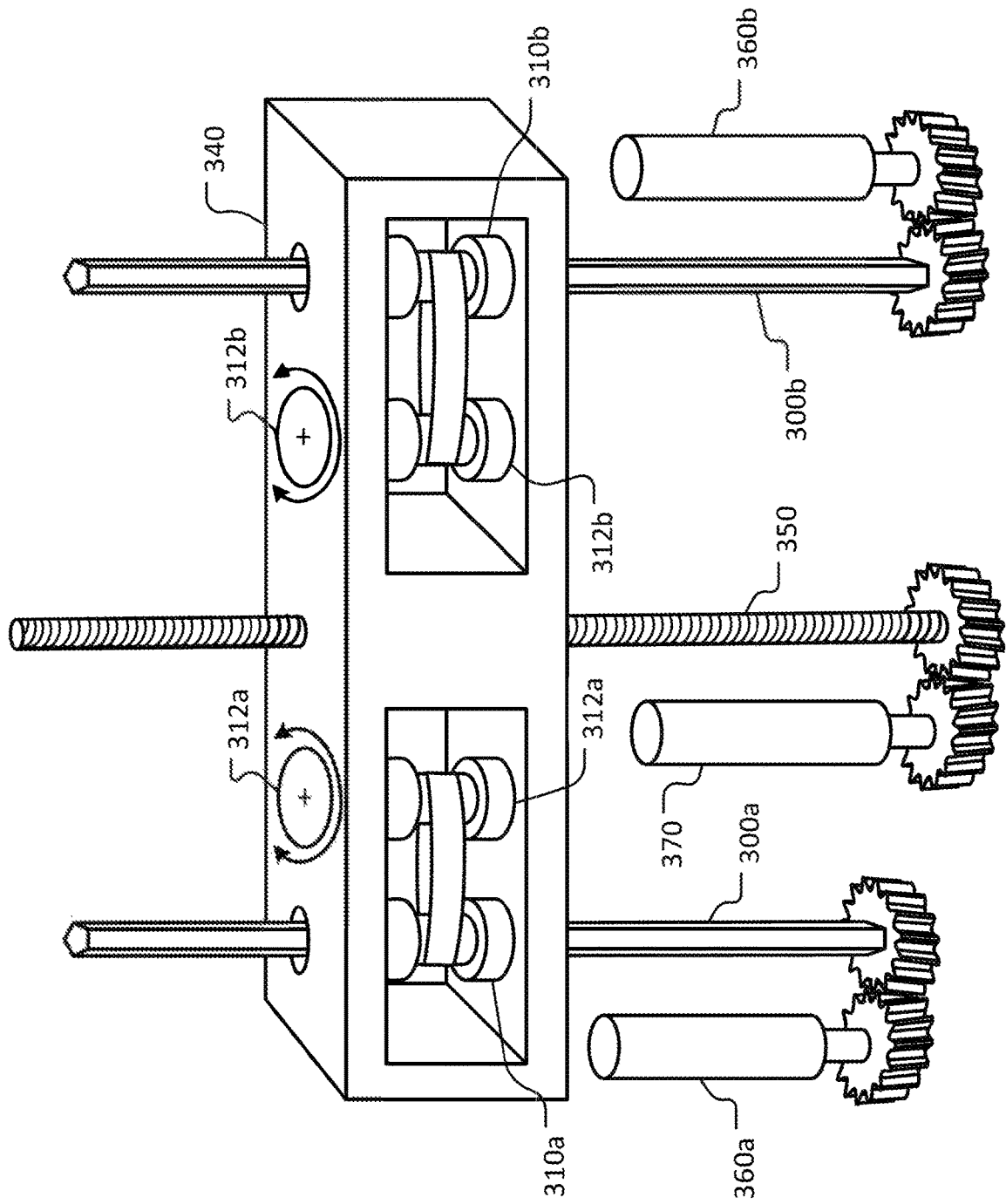
FIG. 21 schematically illustrates an example instrument actuator mechanism that utilizes spline shafts and collars in accordance with some embodiments.

Referring to FIG. 21, the example mechanism illustrated in FIG. 20 can be further embellished in various ways, such as in the depicted example. Here, the spline shaft 300a is rotatably driven by a drive motor 360a, and the spine shaft 300b is rotatably driven by a drive motor 360b. Further, the leadscrew 350 is rotatably driven by a drive motor 370. As shown, the couplings between the drive motors and the driven members can include, in some cases, a one or more transmission components such as gears or other power transmission components.

The illustrated mechanism also includes instrument drive outputs 312a-b. The instrument drive outputs 312a-b are rotatably driven by a respective collar 310a/b. In the depicted embodiment, the instrument drive outputs 312a-b and the collars 310a-b are rotatably coupled using belts. However, any suitable drive coupling technique can be used such as, but not limited to, cables, gears, and the like. When one or more of the drive motors 360a-b are activated, rotations of the respective instrument drive output(s) 312a/b will result. As shown, in some embodiments the instrument drive outputs 312a-b can be positioned on the carriage 340 such that an instrument with corresponding drive input couplings can be coupled to the carriage 340 so that the instrument can receive rotary drive motions from the instrument drive outputs 312a-b.

The illustrated mechanism can be implemented in various beneficial arrangements and configurations. Moreover, the number of spline shafts/collars and/or leadscrews can be varied to meet the needs of a particular implementation, while remaining within the scope of this disclosure.

FIGS. 22 and 23 illustrate an example instrument actuator 360 that uses the spline shaft/collar and leadscrew mechanism concepts described above. The instrument actuator 360 can be implemented, for example, in the context of the instrument actuator 176 described above (see e.g., FIGS. 2 and 7) for computer-assisted surgical systems that utilize robotic technology, and for other uses. The instrument actuator 360 can be coupled, for example, with a manipulator arm (such as the manipulator arm 174). FIG. 23 shows a top view of an upper portion of the instrument actuator 360.

In general, the instrument actuator 360 includes a housing 362 that encloses multiple drive motors (not visible) that are mechanically coupled to individually drive a corresponding spline shaft 300a-e or leadscrew 350a-b. A cannula 180 is releasably coupleable to the housing 362. A carriage 340 is movably coupled to the housing 362, and is threadedly coupled to the leadscrews 350a-b so that the carriage 340 can be driven by rotations of the leadscrews 350a-b along a longitudinal axis 361 (insertion axis) of the instrument actuator 360.

Multiple instrument drive outputs 312a-e are rotatably coupled to the carriage 340. The instrument drive outputs 312a-e are each individually driven by a corresponding spline shaft 300a-e (via a corresponding collar, not visible), which is in turn driven by a corresponding drive motor within the housing 362.

Figure 24:
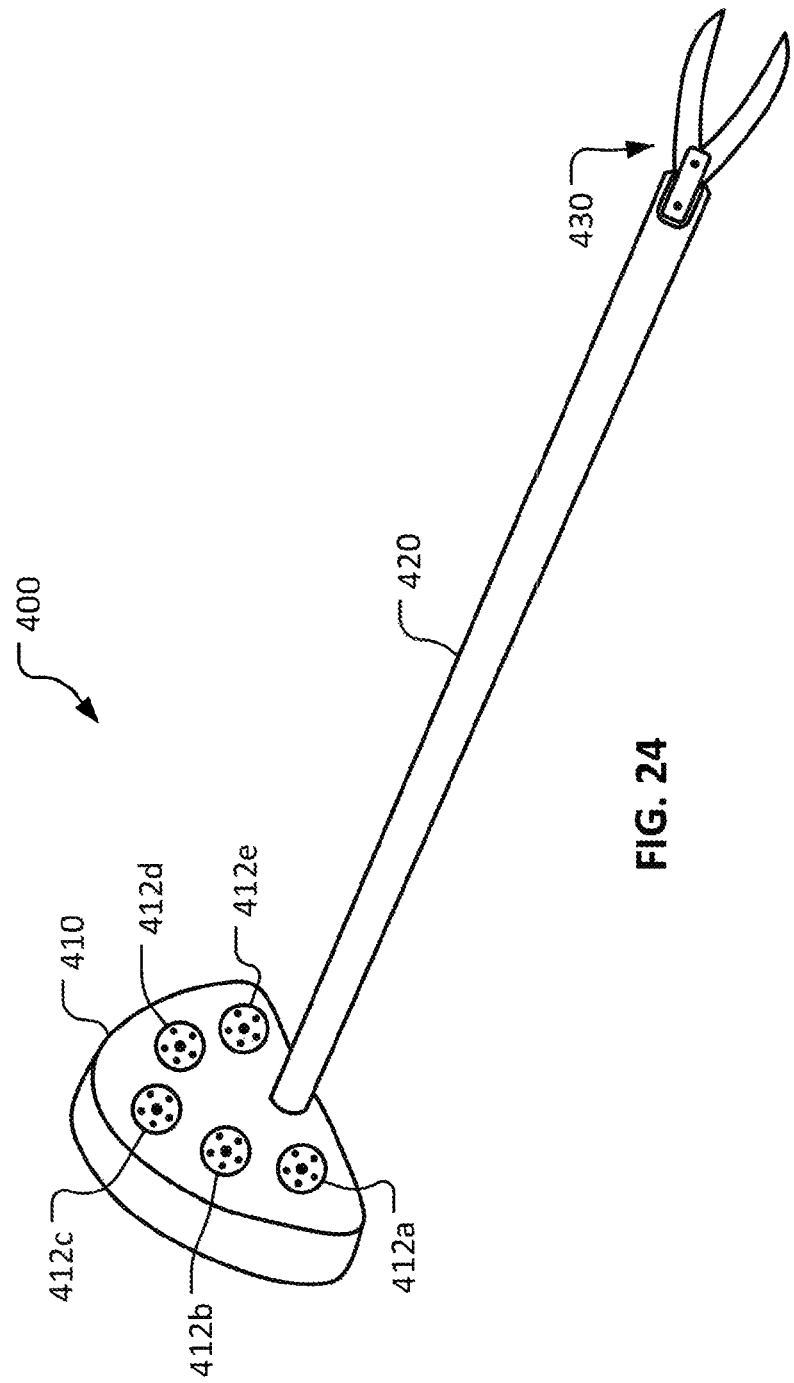
FIG. 24 is a perspective view of an instrument configured for releasably coupling with the instrument actuator of FIG. 22.

Referring also to FIG. 24, the instrument drive outputs 312a-e are positioned on the carriage 340 so as to be accessible to couple with corresponding drive input couplings 412a-e of an instrument 400, in the event that the instrument 400 is coupled to the carriage 340. That is, when a proximal end portion 410 of the instrument 400 is abutted against the carriage 340, the instrument drive outputs 312a-e on the carriage 340 can each releasably couple with a corresponding drive input coupling 412a-e of the instrument 400. In that manner, rotational motion from the drive motors that drive the spline shafts 300a-e is transferred to the instrument 400 to actuate various different movements/ actions of an end effector 430 of the instrument 400. While the depicted embodiment includes five instrument drive outputs 312a-e and corresponding instrument drive inputs 412a-e, in some embodiments one, two, three, four, six, seven, eight, or more than eight instrument drive output/input combinations are included.

In some embodiments, the proximal end portion 410 of the instrument 400 includes a latch mechanism so that the instrument can be securely but removably attached to the carriage 340. Accordingly, as the carriage 340 is driven by the leadscrews 350a-b to translate along the axis 361, an attached instrument 400 will also translate proximally and/or distally along the axis 361. In such an arrangement, a shaft 420 of the instrument 400 slidably extends through a lumen defined by the cannula 180.

Figure 25:
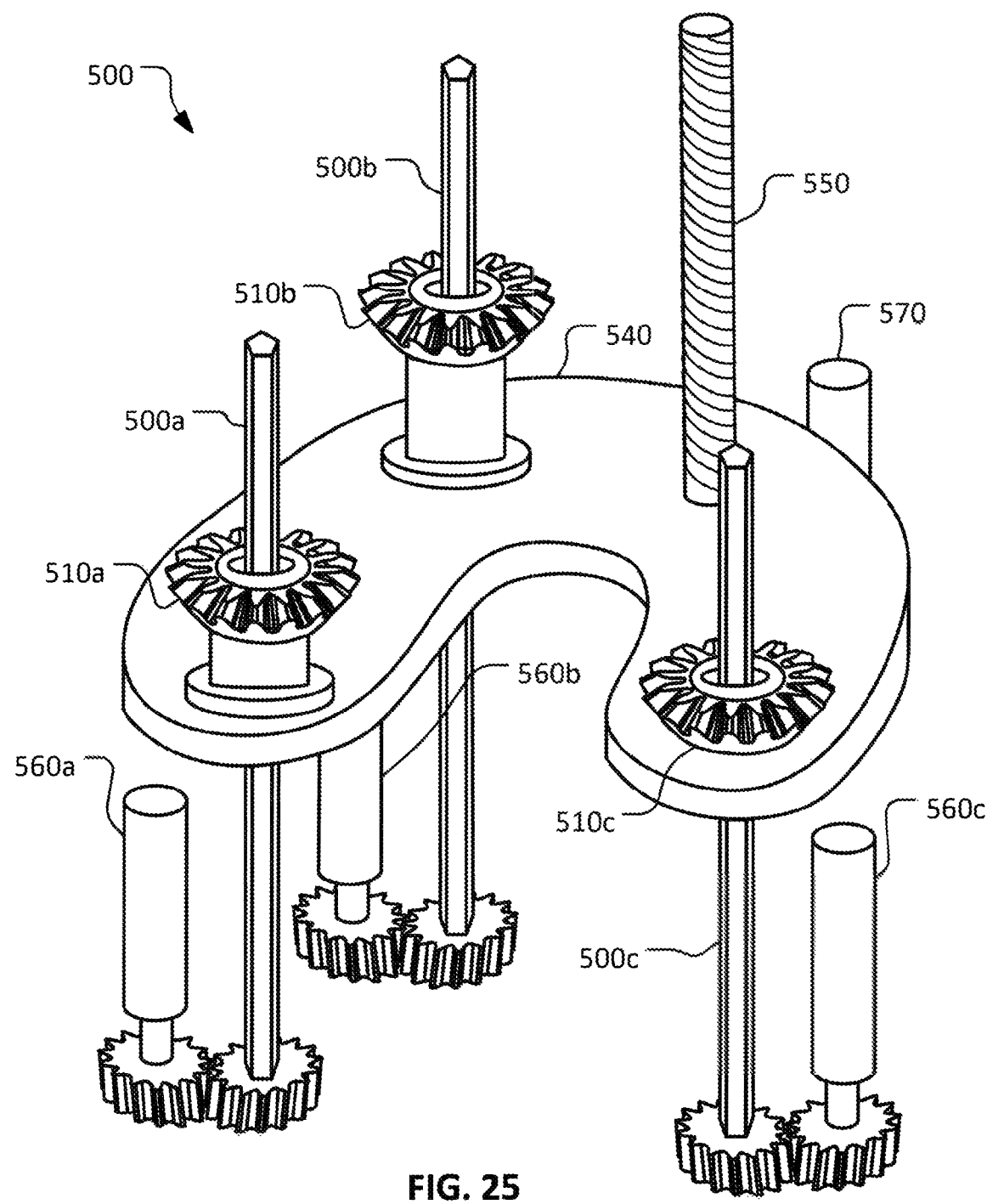
FIG. 25 schematically illustrates another example instrument actuator mechanism that utilizes spline shafts and collars in accordance with some embodiments.

FIG. 25 illustrates another type of example mechanism 500 that uses spline shafts, collars, a leadscrew, and a carriage. Here, three spline shafts 500a-c are each slidably mated with a corresponding collar 510a-c. The three spline shafts 500a-c are each rotatably driven by a corresponding drive motor 560a-c. The collars 510a-c are individually rotatably coupled to a carriage 540.

In the depicted example embodiment, the collars 510a-c each comprise a bevel gear. In some embodiments, the collars 510a-c comprise ball spline bearings or bushings that slide along the spline shafts 500a-c. In some embodiments, one portion of the collars 510a-c is fixed relative to the carriage 540, while another portion of the collars 510a-c is rotatable relative to the carriage 540. The carriage 540 is threadedly coupled with a leadscrew 550 that is rotatably driven by a drive motor 570.

Figure 26:
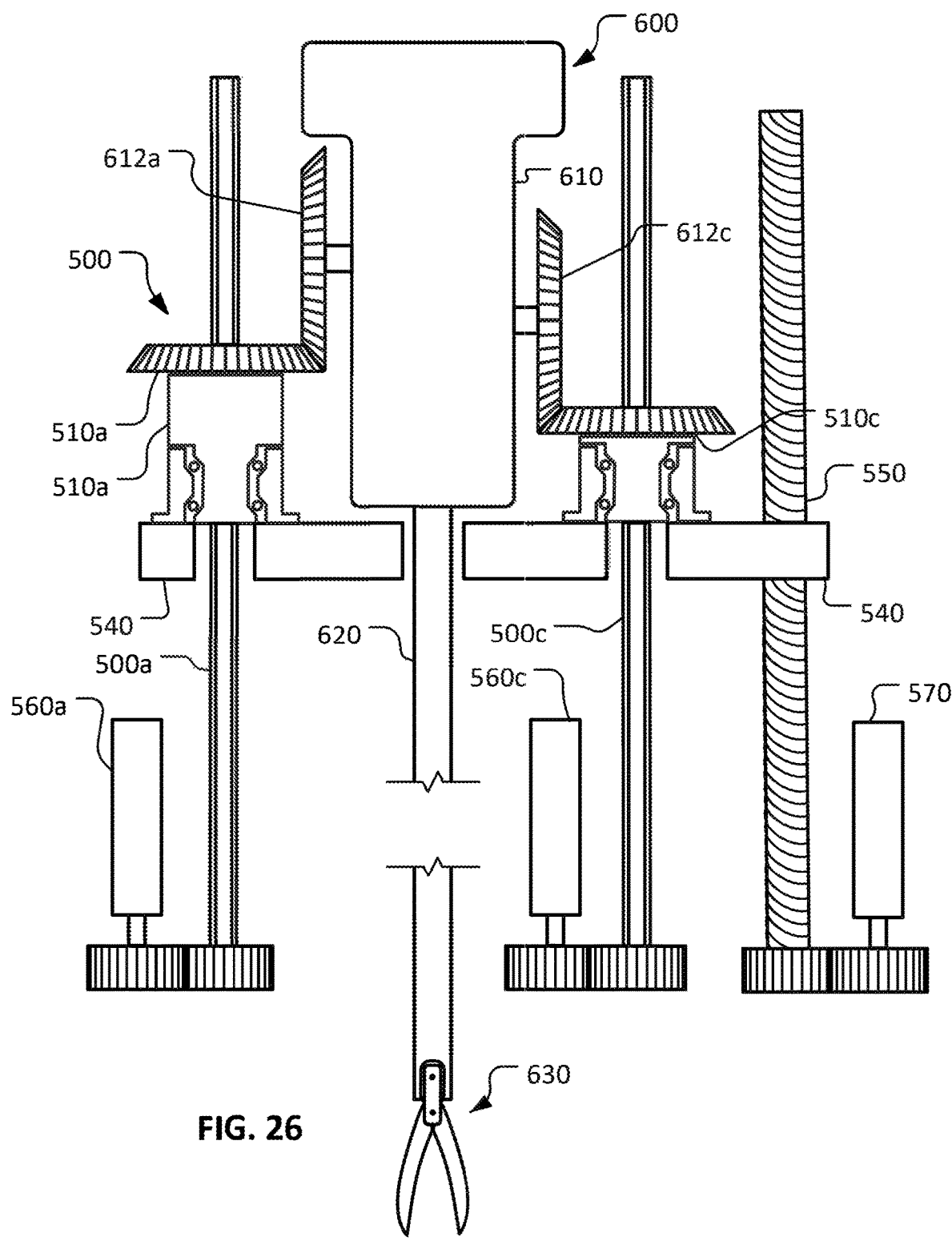
FIG. 26 is a front view of the instrument actuator mechanism of FIG. 25 coupled with an example instrument in accordance with some embodiments.

FIG. 26 schematically shows how the mechanism 500, and/or concepts associated therewith, can be implemented as an instrument actuator (e.g., a surgical instrument actuator). As shown, an example instrument 600 can be releasably coupled with the instrument actuator mechanism 500.

Example instrument 600 includes a proximal end portion 610, an elongate shaft 620, and an end effector 630. A proximal end of the elongate shaft 620 is attached to and extends distally from the proximal end portion 610. The end effector 630 is attached to and extends distally from a distal end of the elongate shaft 620.

In some embodiments, the proximal end portion 610 of the instrument 600 includes a latch mechanism so that the instrument can be securely but removably attached to the carriage 540. The proximal end portion 610 can also include one or more instrument drive inputs. For example, in the depicted embodiment the proximal end portion 610 includes a first instrument drive input 612a, a second instrument drive input 612b (not visible), and a third instrument drive input 612c. In this embodiment, the instrument drive inputs 612a-c comprise bevel gears that individually mesh (releasably couple) with a corresponding bevel gear of collars 510a-c. While the depicted embodiment includes three instrument drive outputs 510a-c and corresponding instrument drive inputs 612a-c, in some embodiments one, two, four, five, six, seven, eight, or more than eight instrument drive output/input combinations are included.

In the depicted embodiment, the bevel gears of the instrument drive inputs 612a-c and the bevel gears of collars 510a-c are at respectively differing distances away from the carriage 540. For example, it can be seen that the instrument drive input 612a and the bevel gear of collar 510a are located farther away from the carriage 540 than the instrument drive input 612c and the bevel gear of collar 510c. Such an arrangement can be beneficial in some embodiments in order to prevent physical interference between the mechanisms associated with the instrument drive inputs 612a-c that are within the proximal end portion 610. For example, in some embodiments the instrument drive inputs 612a-c are coupled to capstans within the proximal end portion 610. One or more cables can be wound around the capstans and, from there, can extend to the end effector 630. Accordingly, the capstans/cables driven by the instrument drive inputs 612a-c can be used to drive adjustments of the various degrees-of-freedom of the end effector 630. With the instrument drive inputs 612a-c and the bevel gears of collars 510a-c at respectively differing distances away from the carriage 540, more room internal to the proximal end portion 610 is provided for the capstans.

Figure 27:
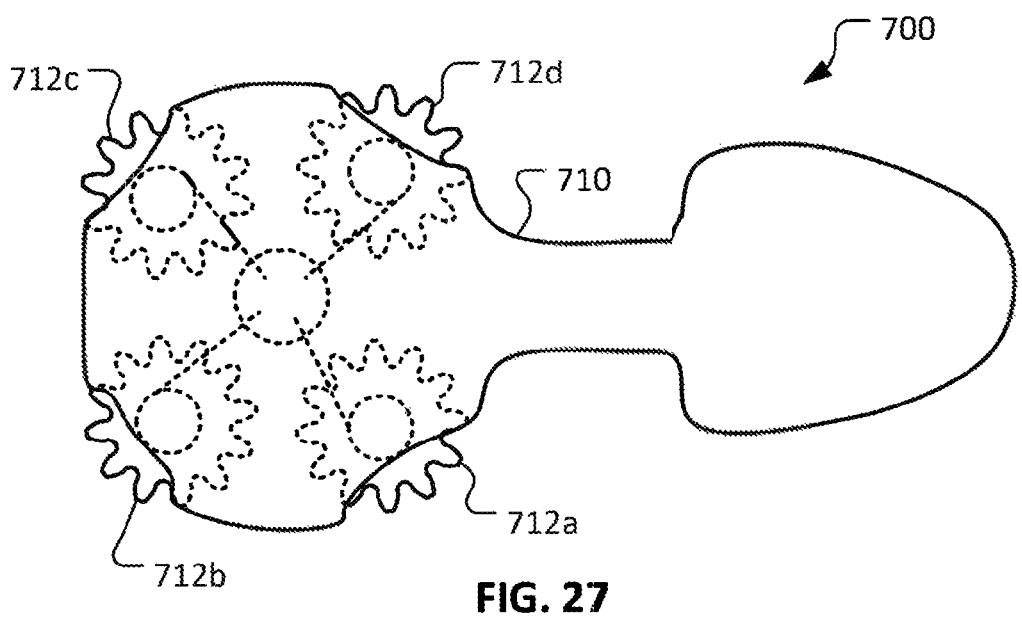
FIG. 27 is a top view of another example instrument in accordance with some embodiments.
Figure 28:
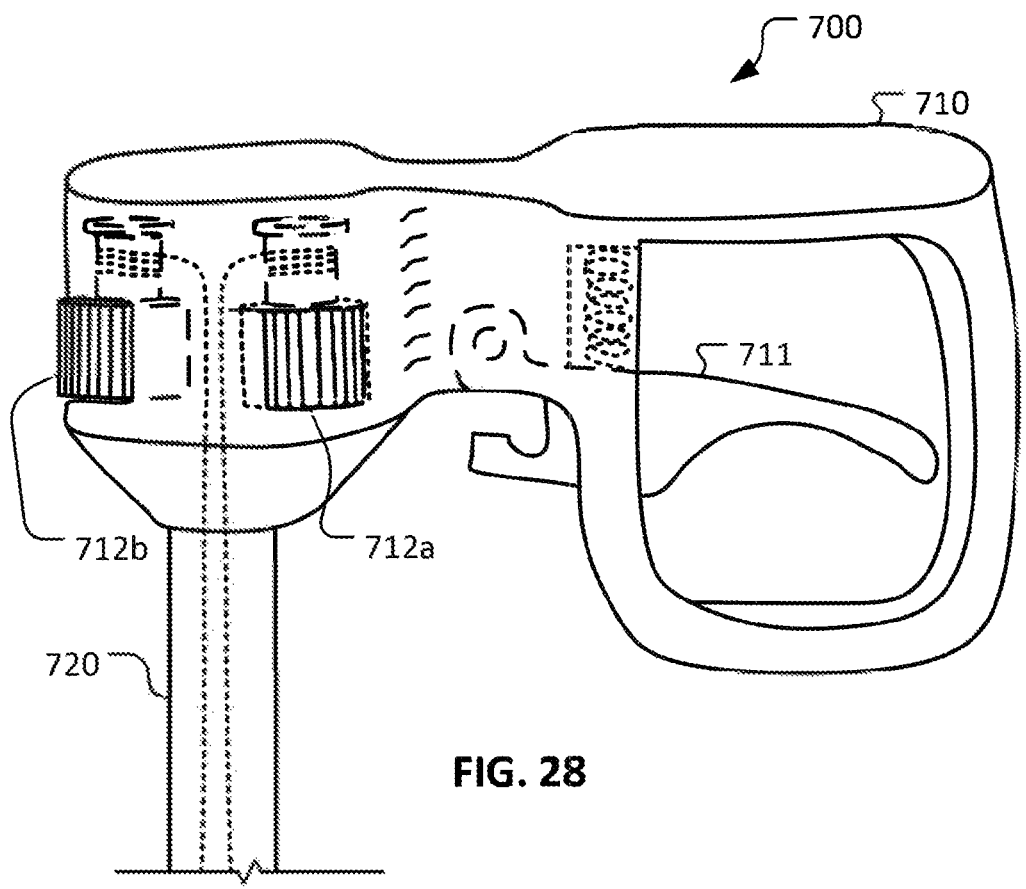
FIG. 28 is a perspective view of a proximal end portion of the instrument of FIG. 27.

Referring to FIGS. 27 and 28, another example instrument 700 (which can be used in some implementations as a surgical instrument, and can be used as a non-surgical instrument in other implementations) can include instrument drive inputs 712a-d that comprise gears. In particular, the depicted embodiment of instrument 700 includes instrument drive inputs 712a-d that individually comprise a respective spur gear (e.g., an involute spur gear). Such spur gears include multiple pairs of adjacent gear teeth between which a valley is defined. The teeth and the valleys of the spur gear instrument drive inputs 712a-d extend parallel to the longitudinal axis of the instrument's shaft 720. While the depicted embodiment uses spur gears for the instrument drive inputs 712a-d, in some embodiment other types of gears, such as bevel gears, can be used.

Each of the instrument drive inputs 712a-d can, for example, drive a capstan and cable arrangement that can adjust/control the degrees-of-freedom of the end effector (not shown) at the distal end of the shaft 720. While the depicted embodiment includes four instrument drive inputs 712a-d, in some embodiments one, two, three, five, six, seven, eight, or more than eight instrument drive inputs combinations are included. In some embodiments, some or all of the instrument drive inputs 712a-d can comprise a torsion spring that tensions the cable(s) to prevent cable slack. In some embodiments, the cable(s) is/are pre-tensioned. While some of the instrument drive inputs 712a-d drive one or more cable(s) using a capstan, one or more of the instrument drive inputs 712a-d can drive a direct activator (e.g., a shaft) for a tool such as a surgical stapler and the like.

The depicted embodiment of the instrument 700 includes a proximal end portion 710 with a handle that comprises a latch mechanism 711 for releasably coupling with a carriage of an instrument actuator. While the handle of the depicted embodiment includes a hoop, in some embodiments no such hoop is included. The instrument drive inputs 712a-d are each configured for individually releasably coupling with a drive output of an instrument actuator (as described further below). In this sense, releasably coupling includes the meshing of a drive gear and a driven gear.

Figure 29:
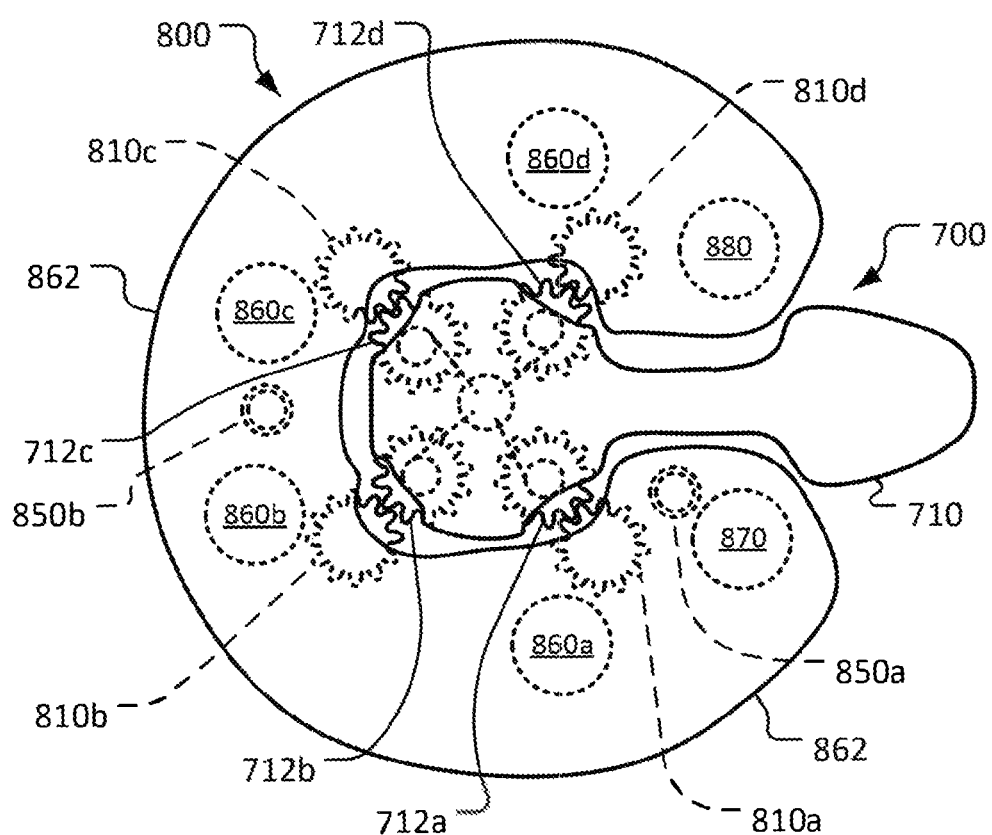
FIG. 29 is a top view of the instrument of FIG. 27 coupled with an example instrument actuator in accordance with some embodiments.

FIG. 29 shows, from a top view, how the instrument 700 can be operatively coupled with an example instrument actuator 800. In this example, the instrument actuator 800 includes a housing 862 that encloses spline shafts 810a-d. In the depicted embodiment, the spline shafts 810a-d have gear-shaped cross-sectional profiles. In other words, the spline shafts 810a-d are elongate spur gears, and/or like spur gear bar stock. Accordingly, the gear-shaped spline shafts 810a-d can mesh with (coupled directly with) the instrument drive inputs 712a-d while allowing sliding contact there between, along the length of the gear-shaped spline shafts 810a-d.

The example instrument actuator 800 includes drive motors 860a-d that each drive a respective one of the spline shafts 810a-d in the manner described above in reference to similar mechanisms. The instrument actuator 800 also includes a first leadscrew 850a and a second leadscrew 850b that are each threadedly coupled with a carriage (not visible) to which the instrument 700 is releasably coupled. A drive motor 870 is rotatably coupled to each of the leadscrews 850a-b as described further below. Accordingly, the drive motor 870 can drive translational movements of the carriage (and of the instrument 700 coupled thereto) distally and proximally along the insertion axis of the instrument 700. The instrument actuator 800 also includes a drive motor 880 that drives rotations of the instrument actuator 800 (and of the instrument 700 coupled thereto) in relation of a manipulator arm to which the instrument actuator 800 is attached. Such rotations can be referred to as "roll."

Figure 30:
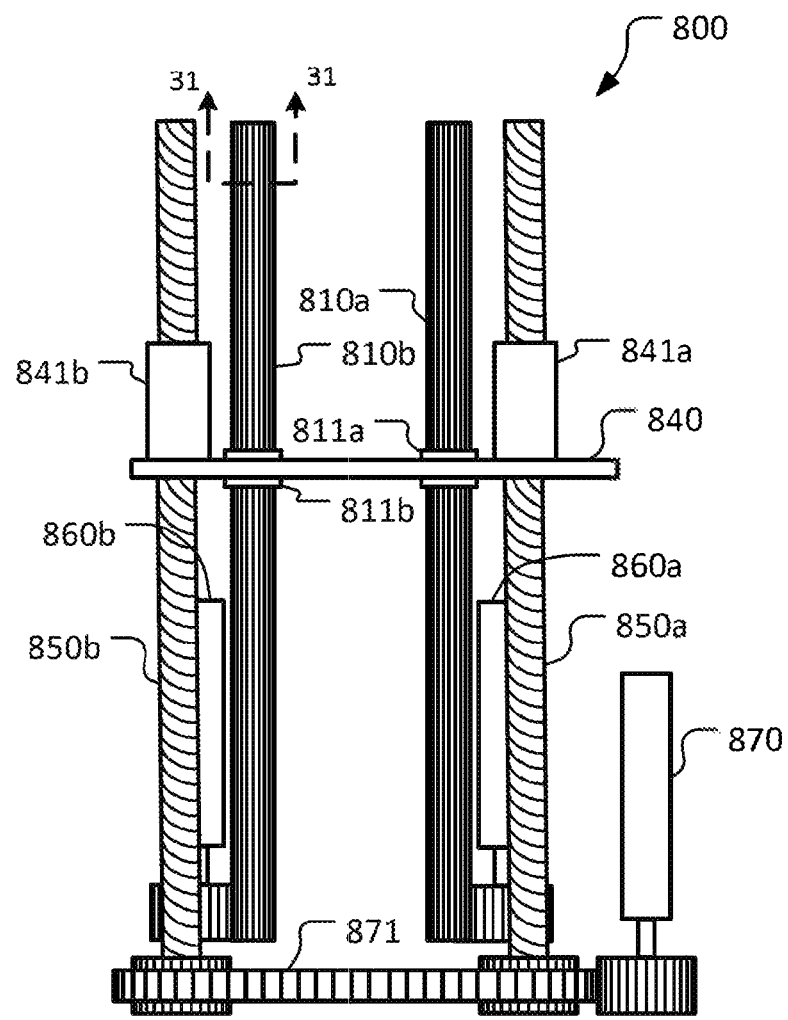
FIG. 30 is a front view of some of the mechanisms of the instrument actuator of FIG. 29.

FIG. 30 shows an elevation view of the example instrument actuator 800 without the housing 862. Here we can see the drive motor 870 that is rotatably coupled to each of the leadscrews 850a-b. In some embodiments, a ring gear 871, belt, timing belt, gear train, and the like can be used to rotatably couple the single drive motor 870 to each of the leadscrews 850a-b. The leadscrews 850a-b are threadedly coupled to the carriage 840 using threaded collars or nuts 841a-b. The carriage 840 slides along the spline shafts 810a-d by virtue of collars 811a-b that may be ball spline bearings, bushings, and the like.

Figure 31:
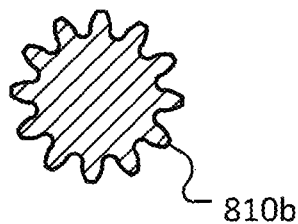
FIG. 31 is a cross-sectional view of a spline shaft of the instrument actuator of FIG. 29.

FIG. 31 shows that a cross-sectional profile of the spline shafts 810a-d is a spur gear shape.

Figure 32:
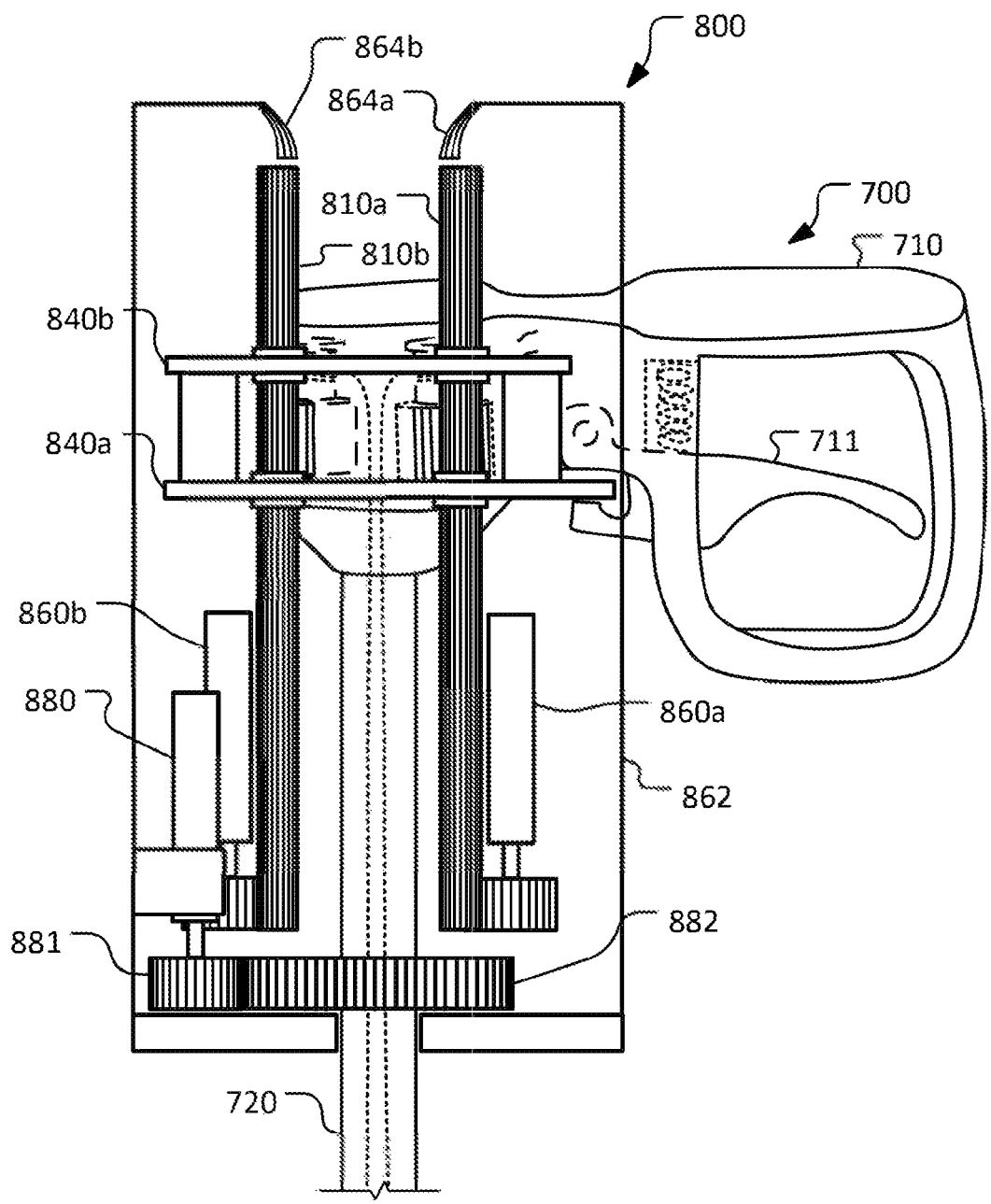
FIG. 32 is a front view of the arrangement of FIG. 29 showing the instrument of FIG. 27 coupled with the instrument actuator of FIGS. 29 and 30.

FIG. 32 schematically shows an elevation view of the instrument 700 coupled with the instrument actuator 800. Here the leadscrews 850a-b are omitted to enhance the clarity of certain other components. The drive motor 880 that drives rotations of the instrument actuator 800 (and of the instrument 700 coupled thereto) in relation of a manipulator arm to which the instrument actuator 800 is attached is visible. In some embodiments, the drive motor 880 is fixedly coupled to the housing 862 and drives a pinion 881 that is meshed with a ring gear 882 fixedly coupled to a manipulator arm (not shown). Accordingly, rotations of the drive motor 880 will cause the entire instrument actuator 800 and instrument 700 assembly to rotate or roll with respect to the manipulator arm.

In the depicted embodiment of the instrument actuator 800, a two-tiered carriage is included. That is, the carriage comprises a first carriage platform 840a and a spaced-apart second carriage platform 840b. The locations of the couplings between the instrument drive inputs 712a-d and the instrument drive outputs (i.e., spline shafts 810a-d) are between the first carriage platform 840a and the second carriage platform 840b. Such an arrangement can help ensure a robust coupling (meshing) between the instrument drive outputs/inputs by inhibiting deflection of the spline shafts 810a-d.

In the depicted embodiment of the instrument actuator 800, lead-in flutes 864a, 864b, 864c (not visible), and 864d (not visible) are included on or near the top (proximal end portion) of the housing 862. The lead-in flutes 864a-d can help facilitate proper alignment of the teeth of the instrument drive inputs 712a-d with the valleys of the spline shafts 810a-d during coupling of the instrument 700 with the instrument actuator 800. In some embodiments, when the instrument 700 is unengaged from the instrument actuator 800, the spline shafts 810a-d are automatically "parked" in alignment with the lead-in flutes 864a-d. Accordingly, easy insertion of the instrument 700 into the instrument actuator 800 can be facilitated using the alignment provided by the lead-in flutes 864a-d relative to the spline shafts 810a-d. Moreover, in some embodiments the ends of the lead-in flutes 864a-d nearest the spline shafts 810a-d can be beveled to facilitate ease of removal of the instrument 700 from the instrument actuator 800. Still further, in some embodiments the proximal end portions of the spline shafts 810a-d can be tapered to ease insertion and/or removal of the instrument 700 relative to the instrument actuator 800.

Figure 33:
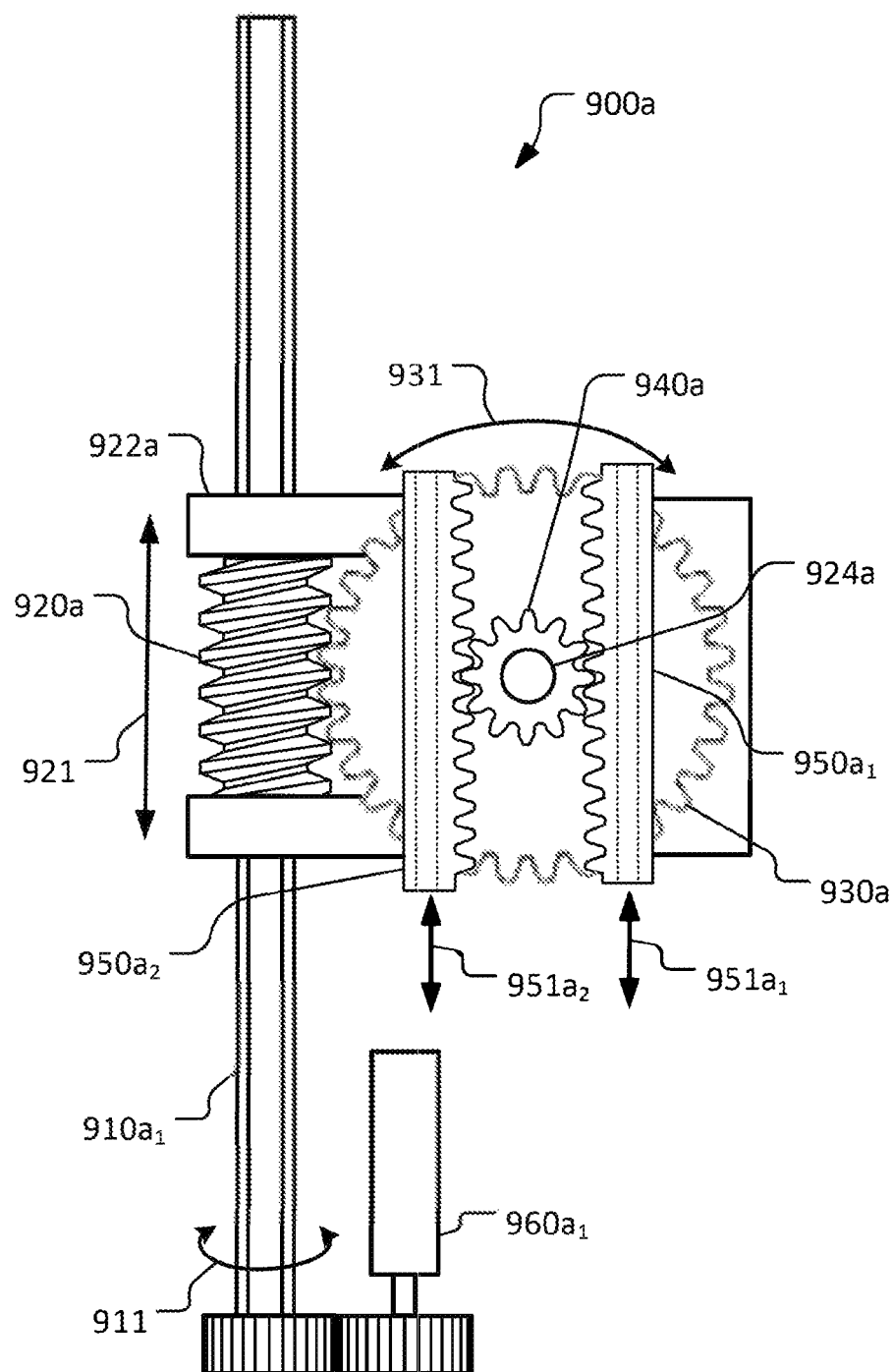
FIG. 33 schematically illustrates another example mechanism that utilizes spline shafts and collars in accordance with some embodiments.

Referring now to FIG. 33, the concepts described above involving spline shafts/collars and the like can be used and expanded on further to obtain various additional innovative designs that can be used in the realm of instrument actuators. For example, the depicted mechanism 900a includes a spline shaft $910a_1$ that is rotatably driven by a drive motor $960a_1$ as represented by arrow 911.

The example mechanism 900a also includes a collar (comprising a worm 920a and a sub-carrier 922a) that is slidably coupled to the spline shaft $910a_1$ as represented by arrow 921. The sub-carrier 922a can also be considered to be a carriage. Rotations of the spline shaft $910a_1$ cause rotations of the worm 920a, but not of the sub-carrier 922a. The worm 920a and sub-carrier 922a are free to translate along the spline shaft $910a_1$.

The example mechanism 900a also includes a worm gear 930a that is rotatably coupled to the sub-carrier 922a using/on a pinion gear axle 924a that is affixed to the sub-carrier 922a. The pinion gear axle 924a extends from the sub-carrier 922a in a lateral direction that is orthogonal to the longitudinal direction defined the spline shaft $910a_1$, and that is orthogonal to the motion of the sub-carrier 922a as represented by arrow 921.

The worm gear 930a is meshed with the worm 920a. When the worm 920a rotates as a result of rotation of the spline shaft $910a_1$, the worm 920a drives rotations of the worm gear 930a around the pinion gear axle 924a as represented by arrow 931. A pinion gear 940a is fixedly attached to the worm gear 930a and is also rotatable in relation to the pinion gear axle 924a. Hence, the pinion gear 940a will rotate along with the worm gear 930a as the worm gear 930a rotates.

The example mechanism 900a also includes two opposing racks, a first rack $950a_1$ and a second rack $950a_2$, that are meshed with the pinion gear 940a. Hence, as the pinion gear 940a rotates, the pinion gear 940a drives the opposing racks $950a_{1-2}$ to translate in opposite directions relative to each other, as represented by arrows $951a_1$ and $951b_2$. The racks $950a_{1-2}$ translate along paths that are parallel to the longitudinal direction defined the spline shaft $910a_1$.

Figure 34:
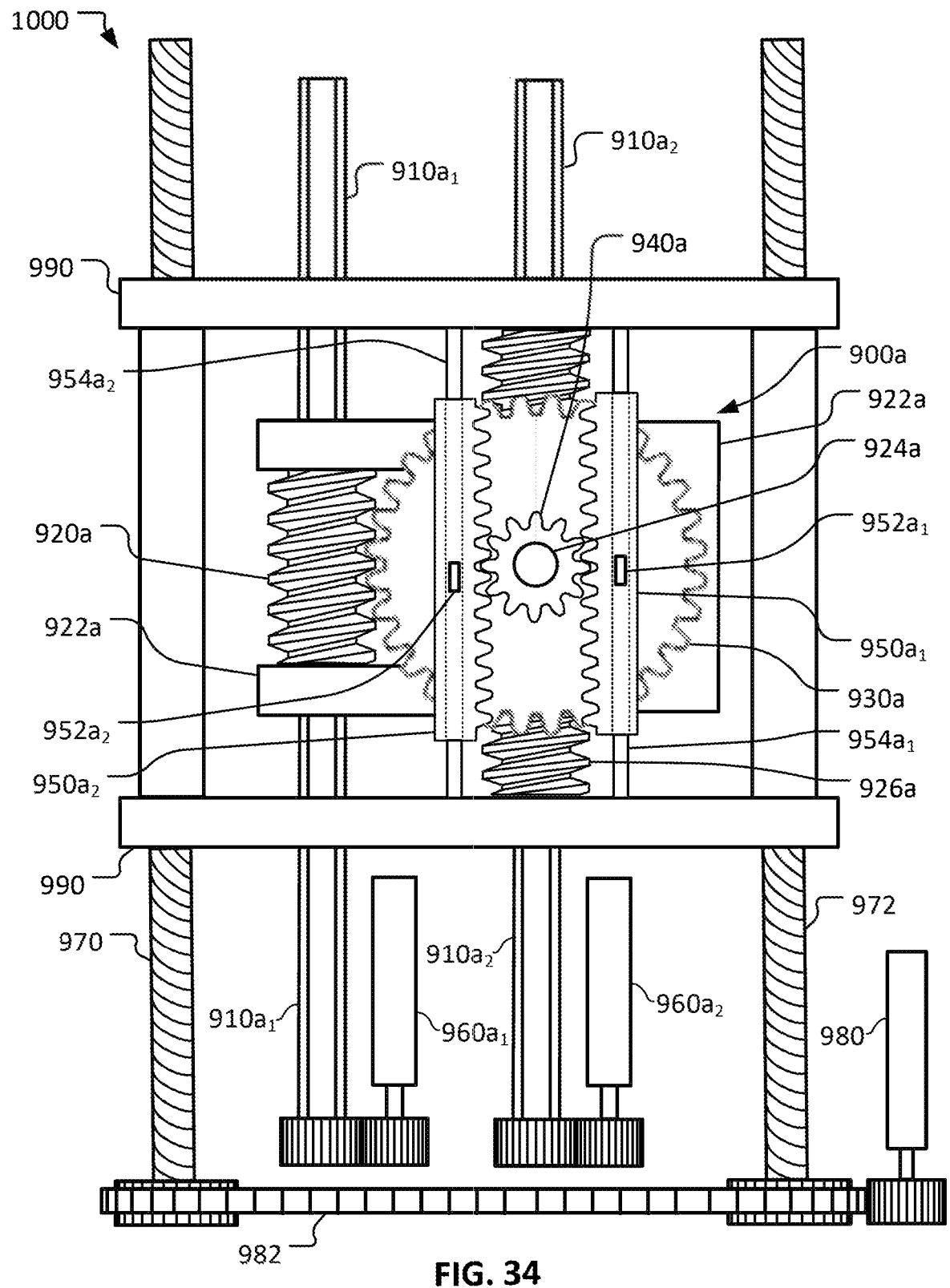
FIG. 34 schematically illustrates another example instrument actuator mechanism that utilizes spline shafts and collars in accordance with some embodiments.

Referring to FIG. 34, the mechanism 900a described above can be included as a sub-assembly in a more extensive mechanism 1000 as shown. In some embodiments, the mechanism 1000 can be implemented as an instrument actuator (e.g., a surgical instrument actuator), or as a portion of an instrument actuator.

In the depicted mechanism 1000, the sub-assembly mechanism 900a is disposed within a two-tiered carriage 990. In some embodiments, the two-tiered carriage 990 comprises an instrument mount, such as a surgical instrument mount. The two-tiered carriage 990 is threadedly coupled with a first leadscrew 970 and a second leadscrew 972. The leadscrews 970 and 972 define the longitudinal direction of the mechanism 1000. For example, in the scenario when mechanism 1000 is used as a surgical instrument actuator, the longitudinal axes of the leadscrews 970 and 972 defines a parallel insertion axis of a surgical instrument coupled to the mechanism 1000.

The leadscrews 970 and 972 are rotatably driven by a drive motor 980 that drives a ring gear 982. The ring gear 982 is meshed with gears coupled to the leadscrews 970 and 972. Accordingly, as the drive motor 980 rotates, the ring gear 982 is rotated, and the leadscrews 970 and 972 are also rotated. Rotations of the leadscrews 970 and 972 cause the two-tiered carriage 990 and the sub-assembly mechanism 900a to translate along the axes of the leadscrews 970 and 972. In some embodiments, a belt, timing belt, cable(s), chain, and the like can be used as an alternative to, or in addition to, the ring gear 982.

As the drive motor 980 drives the two-tiered carriage 990 along the axes of the leadscrews 970 and 972, the two-tiered carriage 990 and the mechanism 900a slidably translate along the spline shafts $910a_1$ and $910a_2$.

The mechanism 1000 also includes the spline shaft $910a_2$. The spline shaft $910a_2$ is rotatably driven by a drive motor $960a_2$. The collar that is slidably mated to the spline shaft $910a_2$ includes the two-tiered carriage 990 and a screw 926a. The screw 926a is coupled to the two-tiered carriage 990 (e.g., captured between the tiers of the two-tiered carriage 990) while still being free to rotate about its longitudinal axis. The screw 926a is threadedly coupled to the sub-carrier 922a (and, in effect, threadedly coupled to the pinion gear axle 924a as a result of the pinion gear axle 924a being affixed to the sub-carrier 922a). Accordingly, as the drive motor $960a_2$ drives rotations of the spline shaft $910a_2$, the screw 926a is caused to rotate and to thereby drive translations of the sub-carrier 922a along the axis of the screw 926a. As the sub-carrier 922a translates in response to the rotations of the screw 926a, the worm 920a, the worm gear 930a, the pinion gear 940a, and the racks $950a_{1-2}$ translate as well.

In the depicted embodiment, the racks $950a_{1-2}$ each translate along a respective shaft or slide $954a_{1-2}$ that extends between the tiers of the two-tiered carriage 990. In some embodiments, the slides $954a_{1-2}$ fixedly couple together the two platform members of the two-tiered carriage 990. The slides $954a_{1-2}$ extend parallel to the leadscrews 970 and 972. Each one of the racks $950a_{1-2}$ is slidably coupled to a respective slide $954a_{1/2}$.

Each one of the racks $950a_{1-2}$ includes a respective instrument drive input engagement feature $952a_{1-2}$. The instrument drive input engagement features $952a_{1-2}$ are positioned and configured to releasably couple with corresponding instrument drive inputs of an instrument that can be releasably coupled to the mechanism 1000, as described further below. In some embodiments, the instrument drive input engagement features $952a_{1-2}$ are protrusions, recesses, cups, detents, and the like.

In some embodiments, one or more load sensors (force sensors) can be included as part of the mechanism 1000. For example, in some embodiments one or more force sensors can be located between the screw 926a and the carriage 900. In some embodiments, one or more force sensors can be arranged to measure the loads applied to the instrument drive input engagement features $952a_{1-2}$.

Figure 35:
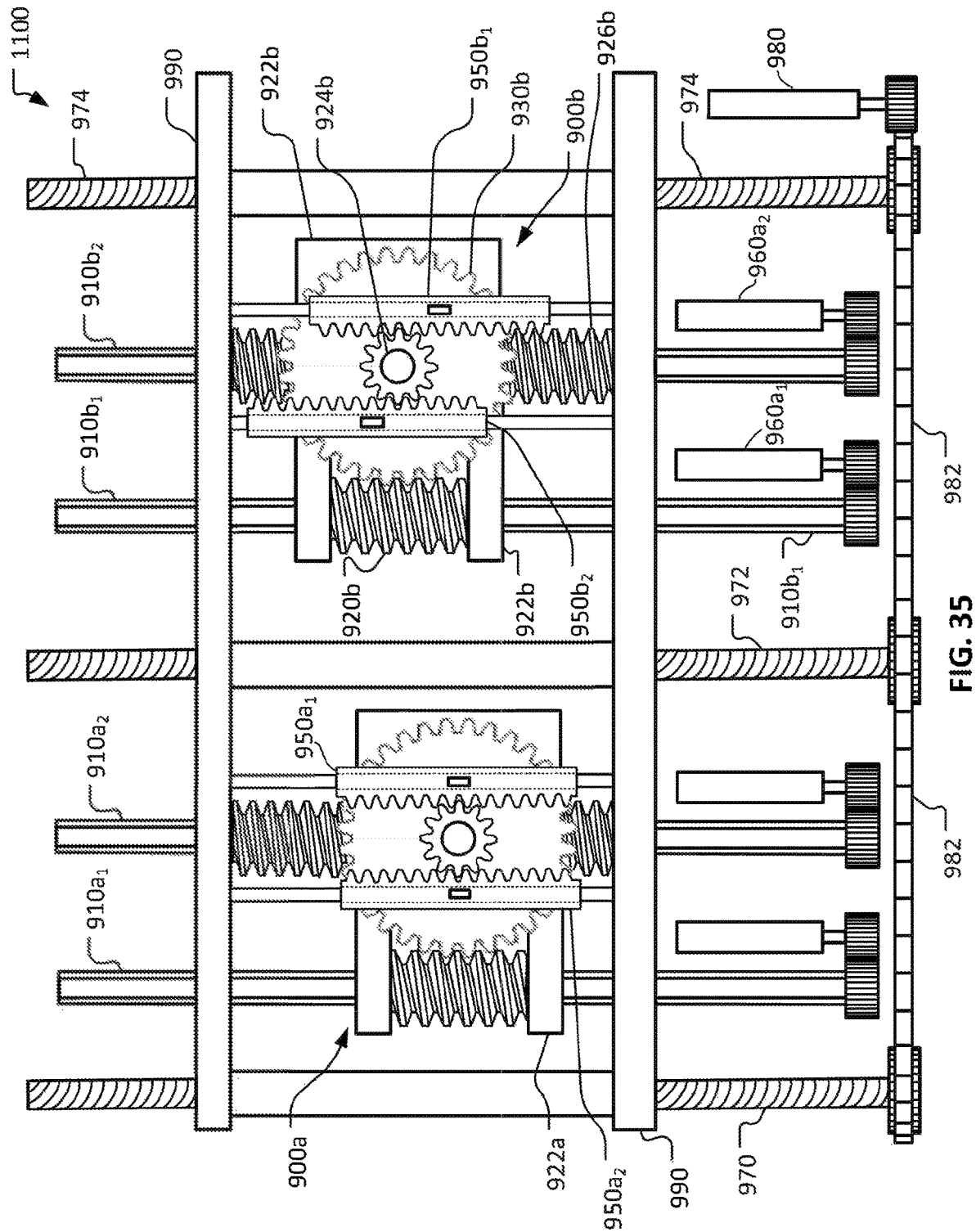
FIG. 35 schematically illustrates another example instrument actuator mechanism that utilizes spline shafts and collars in accordance with some embodiments.

Referring to FIG. 35, the mechanism 1000 and its associated concepts as described above can be incorporated into a more extensive mechanism 1100 as shown. In some embodiments, the mechanism 1100 can be implemented as an instrument actuator (e.g., a surgical instrument actuator), or as a portion of an instrument actuator.

The depicted embodiment of mechanism 1100 includes the components of mechanism 1000. Added to the components of mechanism 1000 are a third leadscrew 974 and a second sub-assembly mechanism 900b. The third leadscrew 974 can be ganged together with and driven in the same manner as leadscrews 970 and 972. The second sub-assembly mechanism 900b can include the same types of components and can be configured the same as the sub-assembly mechanism 900a.

As illustrated by FIG. 35, the first sub-assembly mechanism 900a and the second sub-assembly 900b are independently adjustable/controllable. That concept is illustrated, for example, by the second sub-carrier 922b being shown at a higher elevation than the first sub-carrier 922a. In addition, the racks 950$b_{1-2}$ are shown at differing elevations with respect to each other, while the racks 950$a_{1-2}$ are shown at essentially equal elevations with respect to each other. Such individual adjustability of the first sub-assembly mechanism 900a versus the second sub-assembly 900b is beneficial in the context of controlling multiple degrees of freedom of an instrument that is coupled to the mechanism 1100.

While the mechanism 1100 includes two of the sub-assembly mechanisms 900a and 900b, in some embodiments three, four, five, six, or more than six such sub-assembly mechanisms 900a-b are included in a single mechanism that is configured like the mechanism 1100. Each of the sub-assembly mechanisms can be independently adjustable/controllable.

While some of the mechanisms and associated concepts have been illustrated schematically in the preceding figures, in the following FIGS. 36-42 the mechanisms and associated concepts are shown in design forms that are readily implementable. Like reference numbers are used to indicate correlations of the components and mechanisms. Hence, the above descriptions apply to the like-numbered components and mechanisms in the following figures.

The mechanisms and associated concepts of FIGS. 36-42 can be implemented in the context of computer-assisted systems using robotic technology. In some such contexts, the computer-assisted systems using robotic technology can be used in a surgical setting, such as for minimally-invasive tele-operated surgical systems. In some such contexts, the computer-assisted systems using robotic technology can be used in non-surgical settings for other uses, such as industrial uses.

Figure 36:
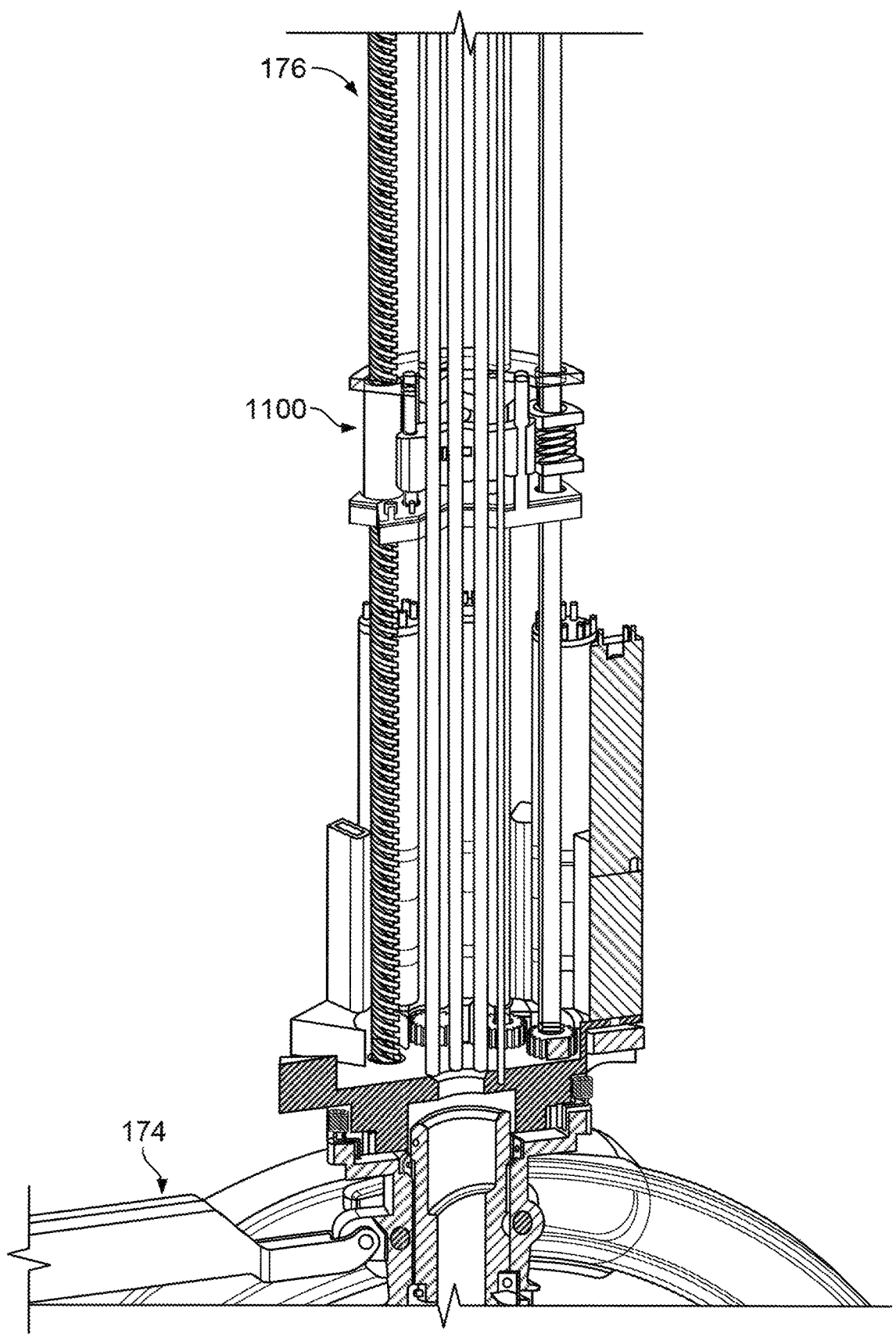
FIG. 36 is a longitudinal cross-sectional perspective view of an example manipulator arm and instrument actuator in accordance with some embodiments.
Figure 37:
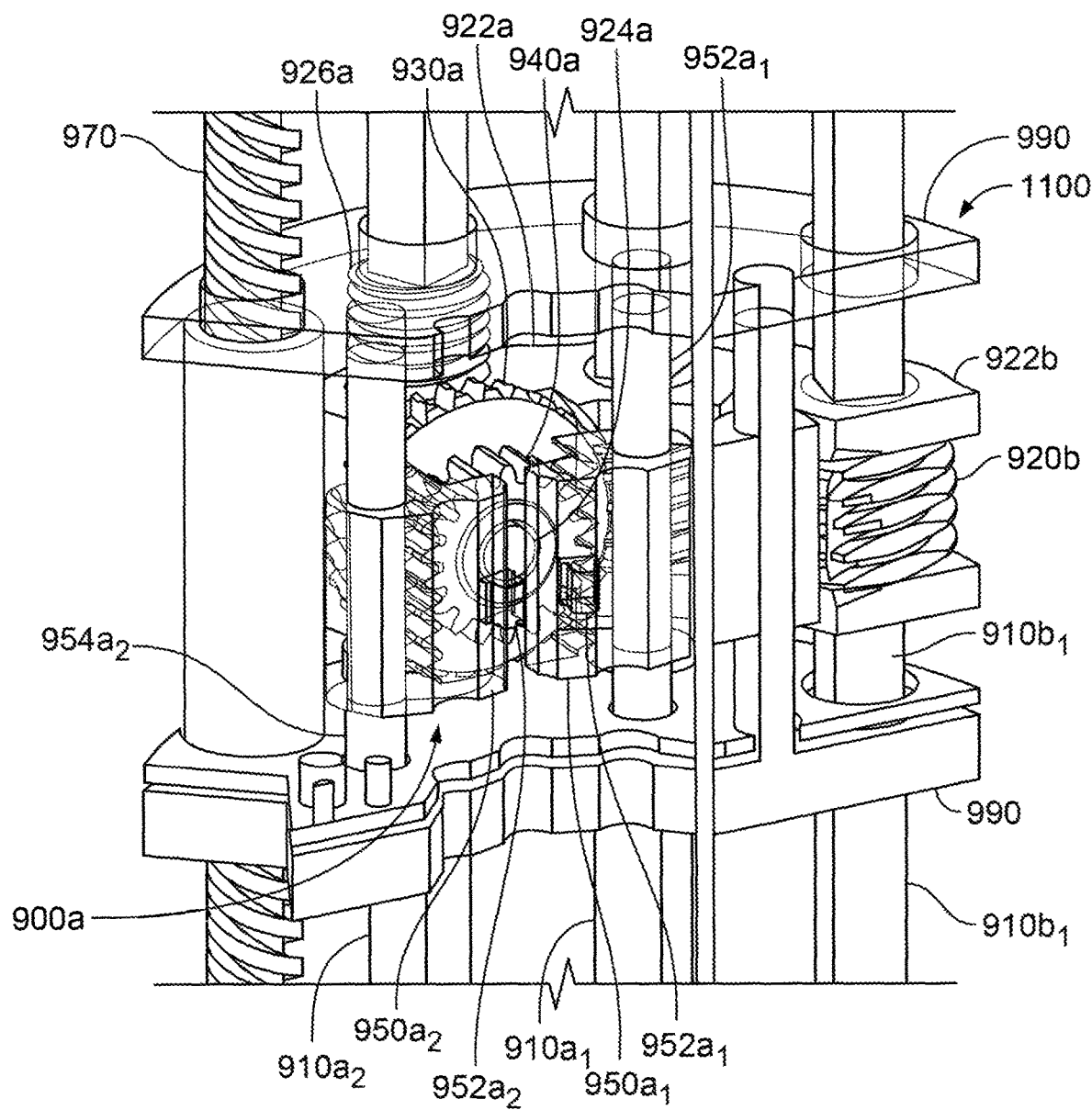
FIG. 37 is an expanded view of a portion of the instrument actuator of FIG. 36.

Referring to FIGS. 36 and 37, the example manipulator arm 174 and instrument actuator 176 as described in the preceding figures (e.g., FIGS. 2 and 7) are shown here in longitudinal cross section. In order to make the inner mechanisms of the instrument actuator 176 visible, the housing of the instrument actuator 176 is not shown. In addition, some components of the manipulator arm 174 and instrument actuator 176 are shown transparently for enhanced visibility of other nearby components. In some embodiments, an entirety of the instrument actuator 176 can be motor-driven to rotate (roll) in relation to the manipulator arm 174 around the insertion axis of an instrument (not shown, refer to FIG. 7) that is coupled with the instrument actuator 176.

The mechanism 1100 is shown with its two-tiered carriage 990. The two-tiered carriage 990 can comprise an instrument mount, such as a surgical instrument mount. The two-tiered carriage 990 is threadedly coupled with a first leadscrew 970 and, in some embodiments, one or more other leadscrews (not visible). The leadscrew(s) 970 defines the longitudinal direction of the mechanism 1100. For example, in the scenario when mechanism 1100 is used as a surgical instrument actuator, the longitudinal axes of the leadscrew(s) 970 defines a parallel insertion axis of a surgical instrument coupled to the mechanism 1100.

Within the space between the tiers of the two-tiered carriage 990 is a first sub-assembly mechanism 900a. A portion of a neighboring second sub-assembly mechanism is also visible (e.g., a spline shaft 910$b_1$, a sub-carrier 922b, and a worm 920b of the neighboring second sub-assembly mechanism are visible).

The sub-assembly mechanism 900a includes a first spline shaft 910$a_1$ and a second spline shaft 910$a_2$ that are individually rotatably driven by respective drive motors (not visible). The sub-assembly mechanism 900a also includes a collar comprising a worm 920a (not visible), a sub-carrier 922a, and a screw 926a. The sub-carrier 922a, the worm 920a, and the screw 926a are slidably coupled to the spline shafts 910$a_{1-2}$.

The sub-carrier 922a and the worm 920a are free to translate along the spline shaft 910$a_1$. The sub-carrier 922a and the screw 926a are free to translate along the spline shaft 910$a_2$. Rotations of the spline shaft 910$a_1$ cause rotations of the worm 920a, but not of the sub-carrier 922a. Rotations of the spline shaft 910$a_2$ cause rotations of the screw 926a, but not of the sub-carrier 922a. Rotations of the spline shaft 910$a_2$ cause translations of the sub-carrier 922a because the screw 926a is threadedly coupled with the sub-carrier 922a.

The sub-assembly mechanism 900a includes the worm gear 930a that is rotatably coupled to the sub-carrier 922a using/on a pinion gear axle 924a that is affixed to the sub-carrier 922a. The pinion gear axle 924a extends from the sub-carrier 922a in a lateral direction that is orthogonal to the longitudinal direction defined the spline shaft 910$a_1$, and that is orthogonal to the translational motion of the sub-carrier 922a relative to the two-tiered carriage 990. The worm gear 930a is meshed with the worm 920a. When the worm 920a rotates as a result of rotation of the spline shaft 910$a_1$, the worm 920a drives rotations of the worm gear 930a around the pinion gear axle 924a. A pinion gear 940a is fixedly attached to the worm gear 930a and is also rotatable in relation to the pinion gear axle 924a. Hence, the pinion gear 940a will rotate along with the worm gear 930a as the worm gear 930a rotates.

The example mechanism 900a also includes two opposing racks, the first rack 950$a_1$ and the second rack 950$a_2$, that are meshed with the pinion gear 940a. Hence, as the pinion gear 940a rotates, the pinion gear 940a drives the opposing racks 950$a_{1-2}$ to translate in opposite directions relative to each other. The racks 950$a_{1-2}$ translate along paths that are parallel to the longitudinal direction defined the spline shafts 910$a_{1-2}$ because the racks 950$a_{1-2}$ translate along the slides 952$a_{1-2}$ that are arranged parallel to the spline shafts 910$a_{1-2}$.

Each one of the racks 950$a_{1-2}$ includes a respective instrument drive input engagement feature 952$a_{1-2}$. The instrument drive input engagement features 952$a_{1-2}$ are positioned and configured to releasably couple with corresponding instrument drive inputs of an instrument that is releasably coupled to the mechanism 1100, as described further below. The fact that the instrument drive input engagement features 952$a_{1-2}$ translate in opposite directions can be used to drive motions of an end effector of an instrument that is releasably coupled to the mechanism 1100.

The mechanism 1100 also includes the screw 926a. The screw 926a is coupled to the two-tiered carriage 990 (e.g., captured between the tiers of the two-tiered carriage 990) while still being free to rotate about its longitudinal axis. The screw 926a is threadedly coupled to the sub-carrier 922a (and, in effect, threadedly coupled to the pinion gear axle 924a as a result of the pinion gear axle 924a being affixed to the sub-carrier 922a). Accordingly, as the drive motor 960$a_2$ drives rotations of the spline shaft 910$a_2$, the screw 926a is caused to rotate and to thereby drive translations of the sub-carrier 922a along the axis of the screw 926a. As the sub-carrier 922a translates in response to the rotations of the screw 926a, the worm 920a, the worm gear 930a, the pinion gear 940a, and the racks 950a$_{1-2}$ translate as well.

The translations of the racks 950a$_{1-2}$ (as a result of rotations of the spline shaft 910a$_2$) are in the same direction and for the same distance. Of course, the same is true for the instrument drive input engagement feature 952a$_{1-2}$ that are fixed to the racks 950a$_{1-2}$. The fact that the instrument drive input engagement features 952a$_{1-2}$ translate concurrently in the same direction, and for the same distance, can be used for tensioning the cables of an instrument (e.g., cables that run between the instrument drive inputs and an end effector of the instrument).

In some embodiments, one or more load sensors (force sensors) can be included as part of the mechanism 1100. For example, in some embodiments one or more force sensors can be located between the screw 926a and a tier of the two-tiered carriage 990. In some embodiments, one or more force sensors can be arranged to measure the loads applied to the instrument drive input engagement features 952a$_{1-2}$. Such loads can correspond to the tension applied the cables that run between an instrument's drive inputs and the instrument's end effector.

Figure 38:
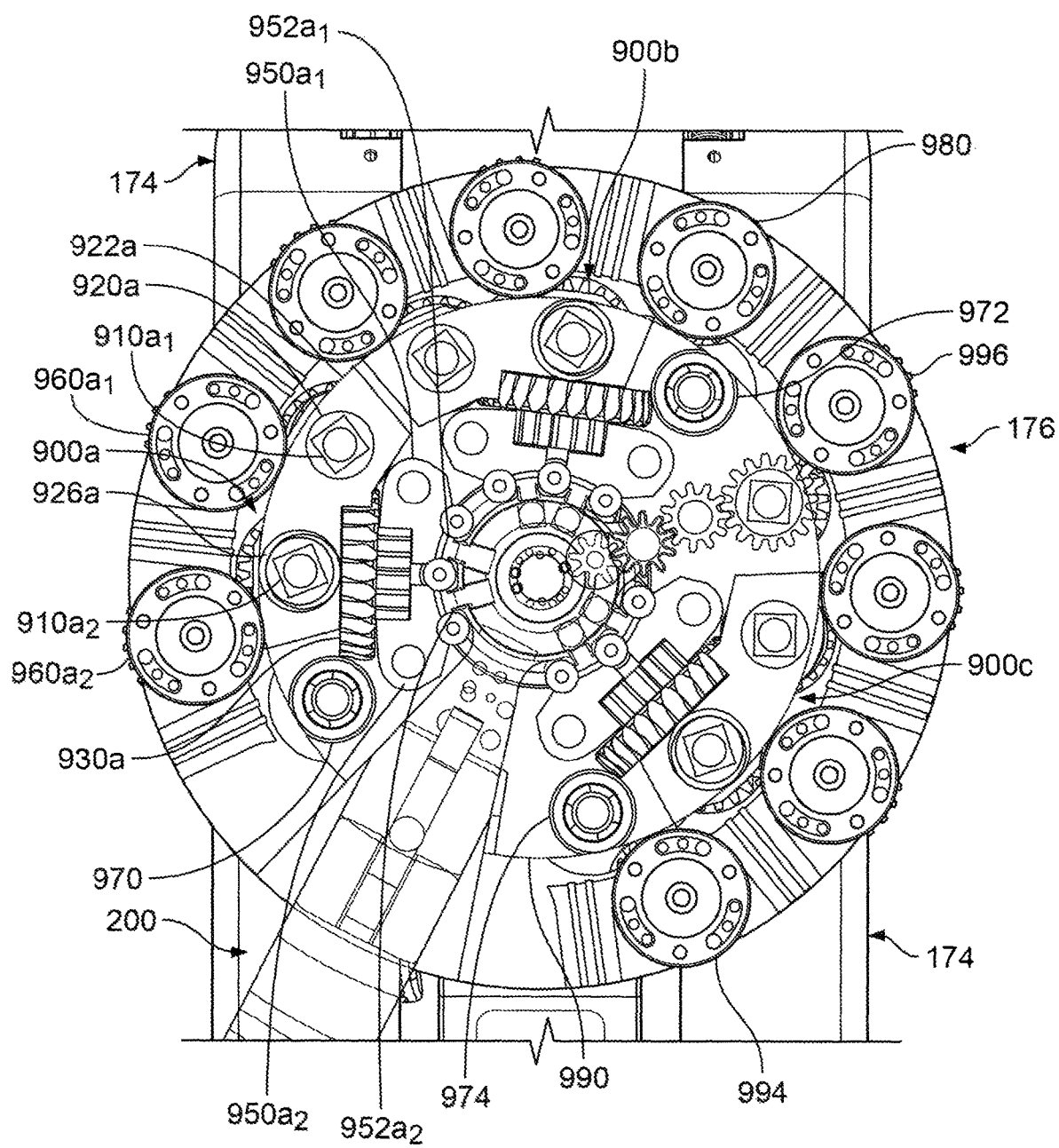
FIG. 38 is a transverse cross-sectional view of the manipulator arm and instrument actuator of FIG. 36.

FIG. 38 shows a cross-sectional top-view of the instrument actuator 176 with an engaged instrument 200 taken along cross-section line 37-37 as shown in FIG. 7. The cross-section is taken just below the upper tier of the two-tiered carriage 990. Hence, three sub-assembly mechanisms 900a, 900b, and 900c, and the lower tier of the two-tiered carriage 990 are visible.

In this cross-sectional view we can see the following labeled components of the sub-assembly mechanism 900a: the spline shafts 910a$_{1-2}$, the drive motors 960a$_{1-2}$, the worm 920a, the screw 926a, the worm gear 930a, the sub-carrier 922a, the racks 950a$_{1-2}$, and the instrument drive input engagement features 952a$_{1-2}$. The other two sub-assembly mechanisms 900b and 900c have analogous components.

Figure 39:
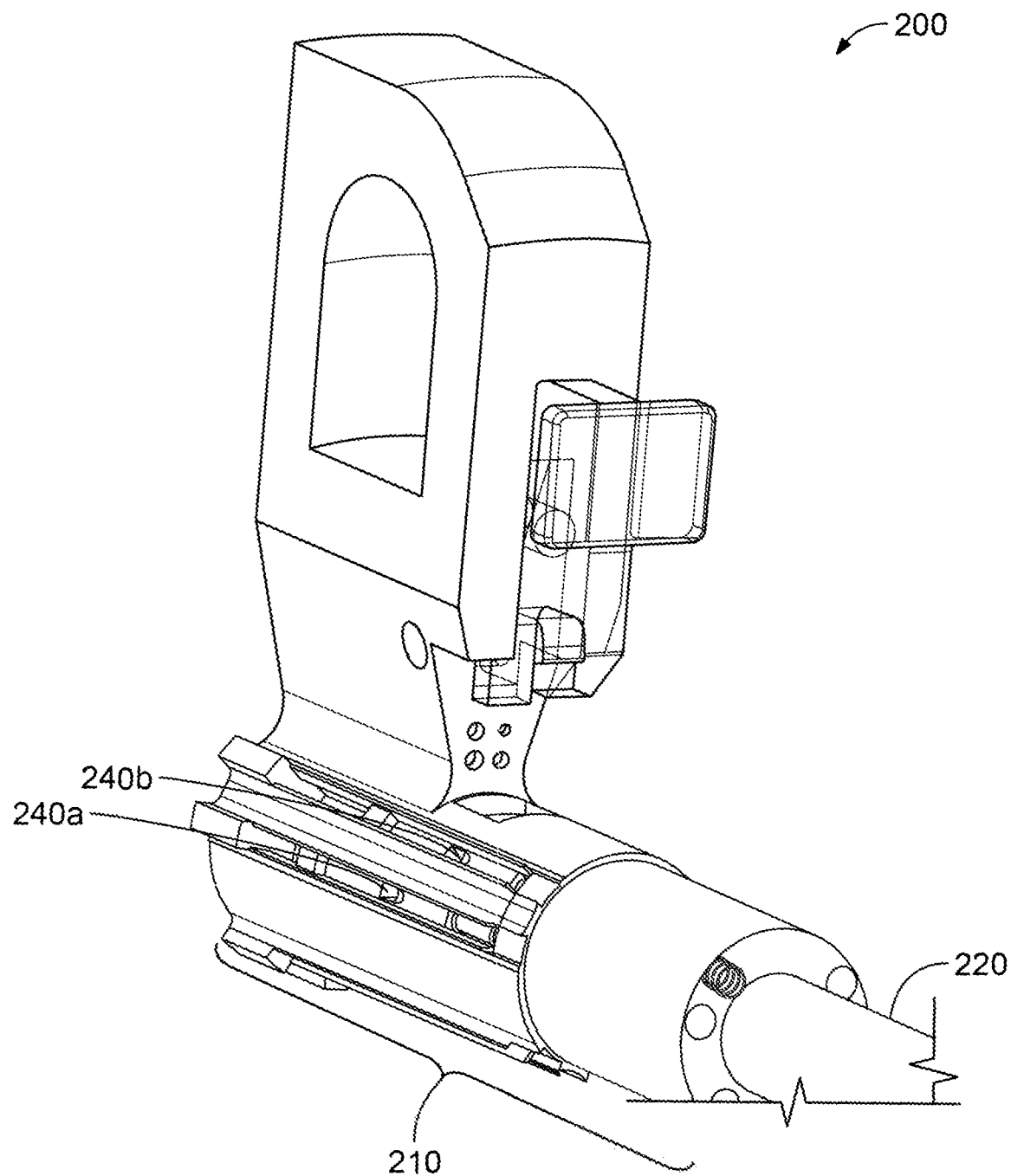
FIG. 39 is a perspective view of a proximal end portion of an example instrument in accordance with some embodiments.

The instrument drive input engagement features 952a$_{1-2}$ (obscured from view) are releasably engaged with corresponding instrument drive inputs of the instrument 200. For example, the instrument 200 can include a pair of instrument drive inputs 240a and 204b as shown in FIG. 39. The instrument drive inputs 240a and 204b can comprise structures (e.g., recesses, protrusions, detents, and the like) that releasably mate with the instrument drive input engagement features 952a$_{1-2}$ of the instrument actuator 176.

In some embodiments, the instrument drive inputs 240a and 204b can be slidingly coupled with the proximal end portion 210 of the instrument 200 so as to be translatable along paths that are parallel to the axis of the elongate shaft 220. In some embodiments, the instrument drive inputs 240a and 240b are coupled to cables that extend from the instrument drive inputs 240a and 240b through the elongate shaft 220 to the end effector.

When the instrument drive inputs 240a and 204b are each translated the same direction, either proximally or distally (e.g., by rotations of the spline shaft 910a$_2$ and the screw 926a), the tension in the cables is increased or decreased respectively. When the instrument drive inputs 240a and 204b are translated in opposite directions relative to each other (e.g., by rotations of the spline shaft 910a$_1$ and the worm 920a), a degree-of-freedom of the end effector of the instrument 200 is adjusted correspondingly.

Still referring to FIG. 38, sub-assembly mechanisms 900b and 900c of the instrument actuator 176 can also include instrument drive input engagement features that are engaged with corresponding instrument drive inputs of the instrument 200. Accordingly, the instrument actuator 176 is configured to drive at least three different degrees-of-freedom of an end effector of the engaged instrument 200, and to control tensions of the cables.

The instrument actuator 176 also includes the drive motor 980 that drives three leadscrews 970, 972, and 974 in the depicted embodiment. The leadscrews 970, 972, and 974 cause the two-tiered carriage 990 to translate along the insertion axis of the instrument 200 when driven by the drive motor 980. The instrument 200 coupled to the two-tiered carriage 990 will also translate distally and/or proximally in response to actuation of the drive motor 980.

The instrument actuator 176 also includes a drive motor 994 that, when actuated, causes the instrument actuator 176 and the instrument 200 to revolve or roll relative, to the manipulator arm 174, around the insertion axis of the instrument 200. In some embodiments, an entirety of the instrument actuator 176 rolls around the insertion axis in response to actuation of the drive motor 994.

Figure 40:
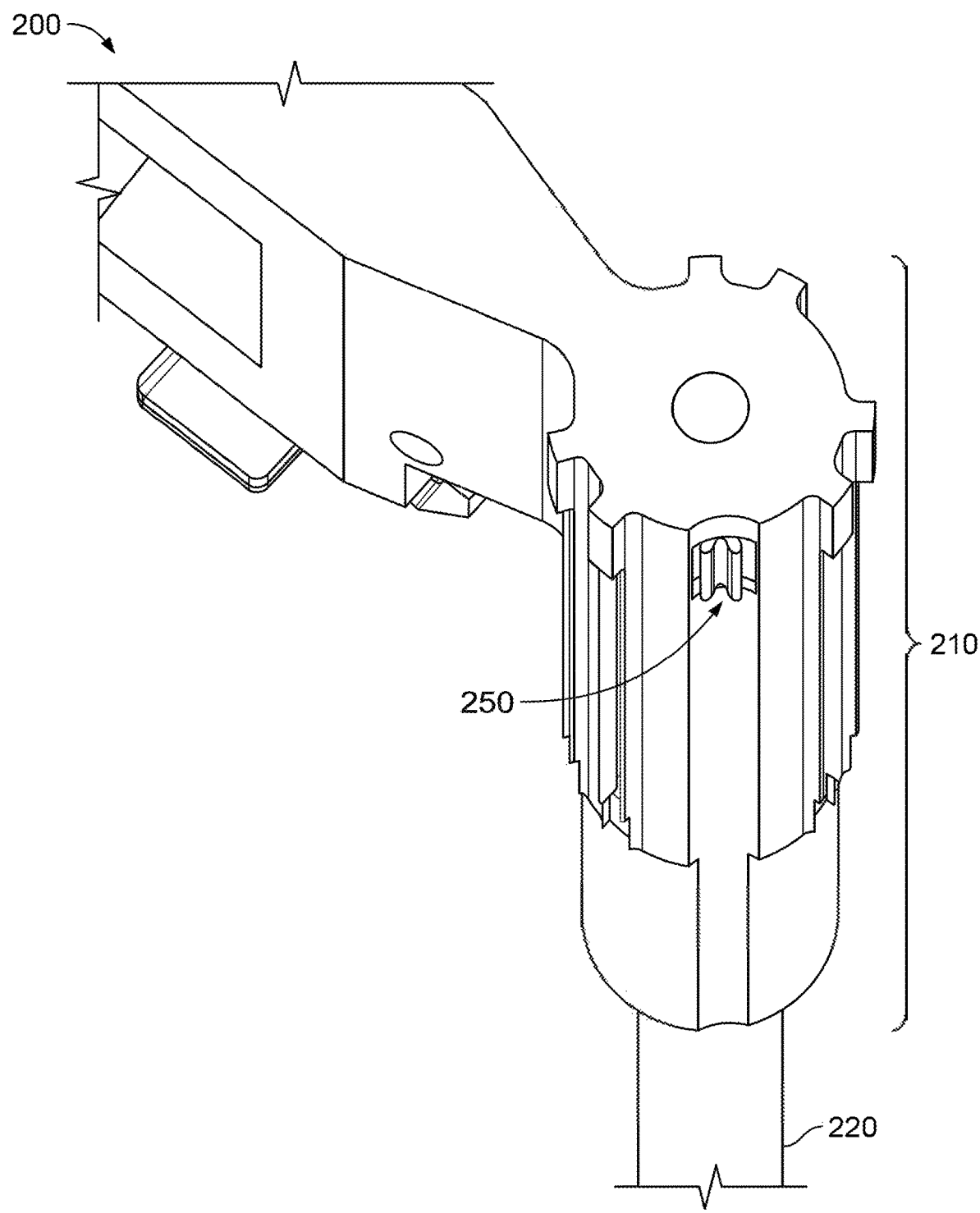
FIG. 40 is another perspective view of a proximal end portion of an example instrument in accordance with some embodiments.

In some embodiments, the instrument actuator 176 also includes a drive motor that can bi-directionally drive another degree-of-freedom of the instrument 200. For example, in the depicted embodiment the instrument actuator 176 includes a drive motor 996 that can drive a gear train that can be used for various purposes such as, but not limited to, staple firing, knife firing, and other operations by the end effector of the instrument 200. Accordingly, in some embodiments the instrument 200 can include an instrument drive input that comprises a gear 250, as shown in FIG. 40 that can mesh with the gear train that is driven by the drive motor 996.

Figure 41:
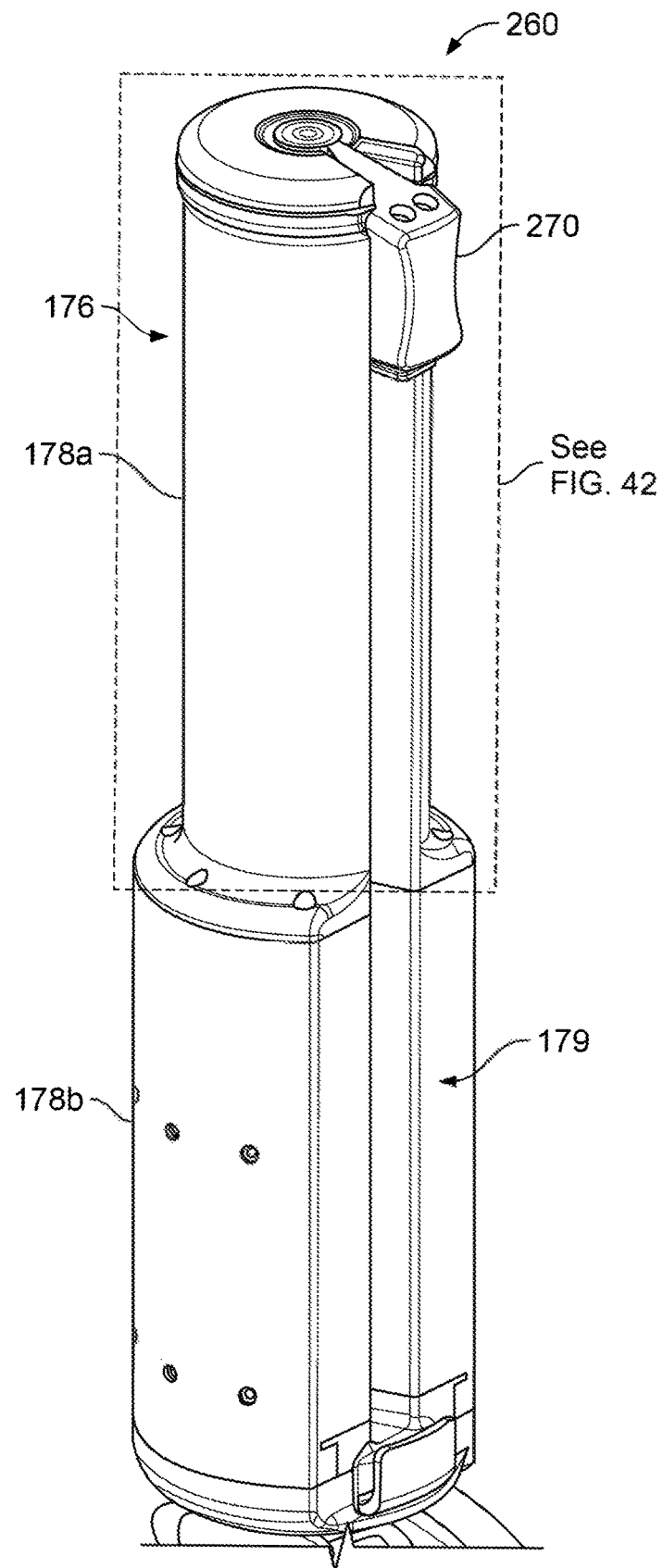
FIG. 41 is a perspective view of an example instrument actuator coupled with an example instrument in accordance with some embodiments.
Figure 42:
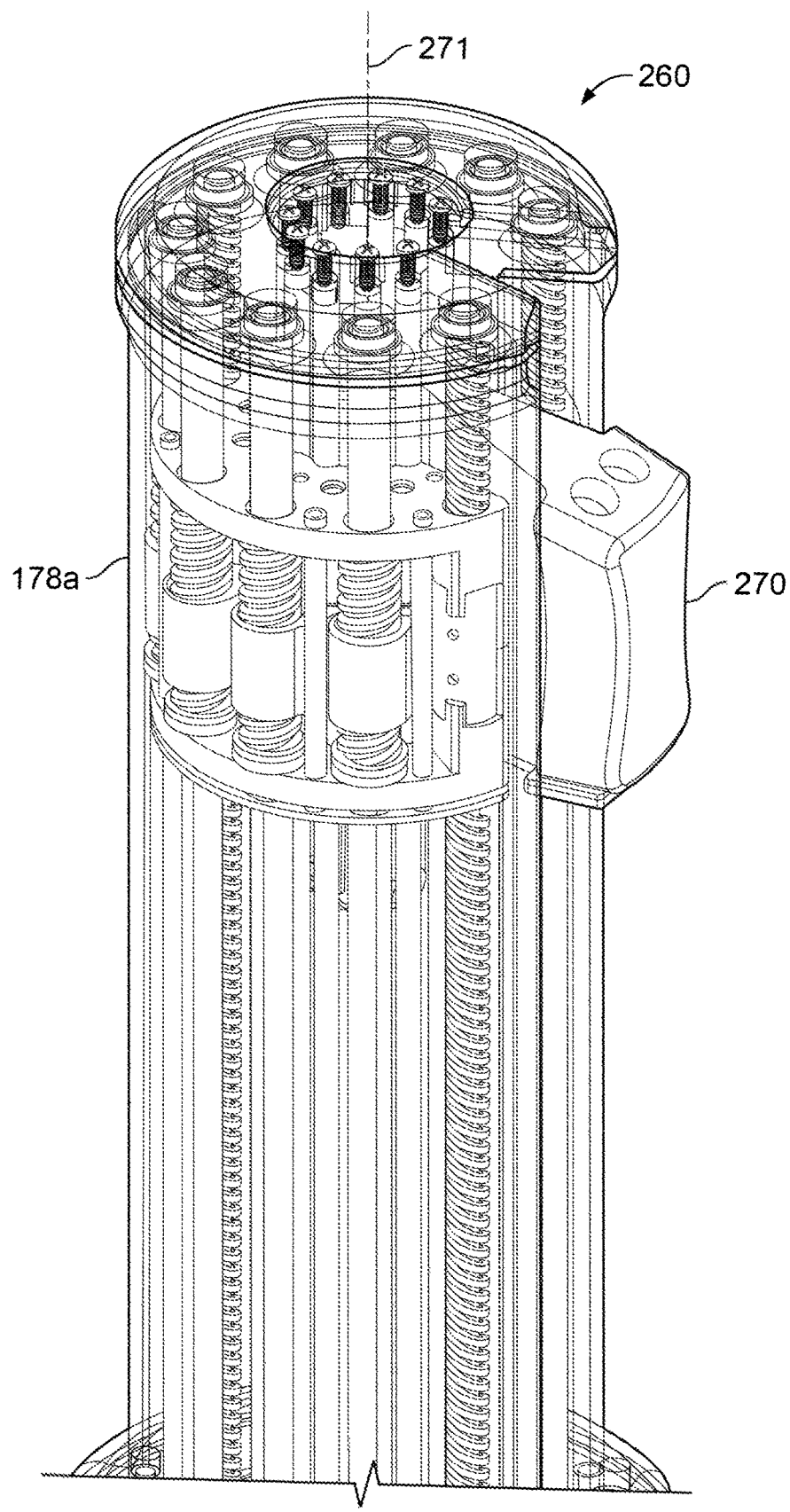
FIG. 42 is a perspective view of a proximal end portion of the coupled instrument actuator and instrument of FIG. 41, with the housing of the instrument actuator shown transparently.

Referring to FIGS. 41 and 42, in some embodiments an instrument 260 that is releasably coupleable with the instrument actuator 176 includes a handle 270 that has a compact profile. The compact handle 270 can be advantageous because the instrument 260 and instrument actuator 176 move around during use and a larger handle can be obstructive in some circumstances.

The instrument actuator 176 includes an outer housing comprising a proximal portion of the outer housing 178a and a distal portion of the outer housing 178b. The outer housing portions 178a-b extend around and along the longitudinal axis 271 (insertion axis) of the instrument 260.

The proximal portion of the outer housing 178a defines an outer boundary/periphery around the longitudinal axis 271. The outer boundary/periphery of the proximal portion of the outer housing 178a is essentially cylindrical.

The distal portion of the outer housing 178b also defines an outer boundary/periphery around the longitudinal axis 271. The outer boundary/periphery of the distal portion of the outer housing 178b defines a maximum outer periphery of the instrument actuator 176. The outer boundary/periphery of the distal portion of the outer housing 178b is not cylindrical. Instead, the cross-sectional shape of the outer boundary/periphery of the distal portion of the outer housing 178b is generally D-shaped. Accordingly, a cutout volume is defined between a flattened side wall 179 of the distal portion of the outer housing 178b and the cylindrical boundary/periphery defined by an extension of the curved (e.g., radiused, arcuate, or a circular segment) wall portion of the distal portion of the outer housing 178b that is radially outward of the flattened side wall 179. In the depicted embodiment, the cutout volume has a D-shaped cross-sectional shape.

In some embodiments, such as the depicted embodiment, the portion of the handle 270 that protrudes radially from the outer boundary/periphery instrument actuator 176 is within the cutout volume of the distal portion of the outer housing 178b. That is, the handle 270 does not radially extend beyond the cutout volume. In contrast, the handle 270 does radially extend beyond the outer boundary/periphery of the proximal portion of the outer housing 178a.

The proximal portion of the outer housing 178a defines a radius from the axis 271. The distance that the handle 270 extends from the axis 271 is greater than the radius of the proximal portion of the outer housing 178a. The distal portion of the outer housing 178b defines a radius from the axis 271 (from the axis 271 to the outer surface of the cylindrical portion of the outer housing 178b). The distance that the handle 270 extends from the axis 271 is less than the radius of the distal portion of the outer housing 178b.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A surgical instrument actuation mechanism comprising:
    a first spline shaft;
    a second spline shaft;
    a carriage translatable along the first and second spline shafts; and
    a screw slidably mated around the second spline shaft and threadedly coupled with the carriage for driving translation of the carriage along the first spline shaft and the second spline shaft.

2. The surgical instrument actuation mechanism of claim 1, further comprising:
    a pinion gear axle extending from the carriage; and
    a pinion gear rotatably coupled to the pinion gear axle.

3. The surgical instrument actuation mechanism of claim 1, wherein the carriage is a second carriage, and wherein the surgical instrument actuation mechanism further comprises:
    a first carriage; and
    a first leadscrew threadedly coupled with the first carriage.

4. The surgical instrument actuation mechanism of claim 3, wherein the first leadscrew extends parallel to a longitudinal axis of the surgical instrument actuation mechanism, and wherein the first carriage translates along the longitudinal axis in response to rotations of the first leadscrew.

5. The surgical instrument actuation mechanism of claim 3, wherein the first carriage comprises:
    a first platform member; and
    a second platform member fixedly coupled to the first platform member in a spaced apart arrangement, and wherein the second carriage is disposed between the first platform member and the second platform member.

6. The surgical instrument actuation mechanism of claim 5, further comprising:
    a first rack meshed with a pinion gear; and
    a second rack meshed with the pinion gear,
    wherein the second platform member is fixedly coupled to the first platform member by slides on which the first rack and the second rack slidably translate.

7. A surgical instrument actuation mechanism comprising:
    a first spline shaft;
    a second spline shaft;
    a carriage translatable along the first and second spline shafts;
    a collar slidably mated with the second spline shaft and threadedly coupled with the carriage;
    a pinion gear axle extending from the carriage; and
    a pinion gear rotatably coupled to the pinion gear axle,
    wherein the collar is a second collar, wherein the surgical instrument actuation mechanism further comprises a first collar slidably mated with the first spline shaft, and wherein the first collar comprises a worm meshed with a worm gear that is coupled to the pinion gear.

8. The surgical instrument actuation mechanism of claim 7, wherein the carriage is a second carriage, and wherein the surgical instrument actuation mechanism further comprises:
    a first carriage; and
    a first leadscrew threadedly coupled with the first carriage.

9. The surgical instrument actuation mechanism of claim 8, wherein the first leadscrew extends parallel to a longitudinal axis of the surgical instrument actuation mechanism, and wherein the first carriage translates along the longitudinal axis in response to rotations of the first leadscrew.

10. The surgical instrument actuation mechanism of claim 8, wherein the first carriage comprises:
    a first platform member; and
    a second platform member fixedly coupled to the first platform member in a spaced apart arrangement, and wherein the second carriage is disposed between the first platform member and the second platform member.

11. The surgical instrument actuation mechanism of claim 10, further comprising:
    a first rack meshed with the pinion gear; and
    a second rack meshed with the pinion gear,
    wherein the second platform member is fixedly coupled to the first platform member by slides on which the first rack and the second rack slidably translate.

12. A surgical instrument actuation mechanism comprising:
    a first spline shaft;
    a second spline shaft;

a carriage translatable along the first and second spline shafts;

a collar slidably mated with the second spline shaft and threadedly coupled with the carriage;

a pinion gear axle extending from the carriage; and a pinion gear rotatably coupled to the pinion gear axle, a first rack meshed with the pinion gear; and a second rack meshed with the pinion gear, wherein the first rack and the second rack are meshed with the pinion gear at diametrically opposite sides of the pinion gear.

13. The surgical instrument actuation mechanism of claim 12, wherein the carriage is a second carriage, and wherein the surgical instrument actuation mechanism further comprises:

a first carriage; and a first leadscrew threadedly coupled with the first carriage.

14. The surgical instrument actuation mechanism of claim 13, wherein the first leadscrew extends parallel to a longitudinal axis of the surgical instrument actuation mechanism, and wherein the first carriage translates along the longitudinal axis in response to rotations of the first leadscrew.

15. The surgical instrument actuation mechanism of claim 13, wherein the first carriage comprises:

a first platform member; and a second platform member fixedly coupled to the first platform member in a spaced apart arrangement, and wherein the second carriage is disposed between the first platform member and the second platform member.

16. The surgical instrument actuation mechanism of claim 15, further comprising:

a first rack meshed with the pinion gear; and a second rack meshed with the pinion gear, wherein the second platform member is fixedly coupled to the first platform member by slides on which the first rack and the second rack slidably translate.

* * * * *